US011857583B2

(12) United States Patent
Lin et al.

(10) Patent No.: US 11,857,583 B2
(45) Date of Patent: Jan. 2, 2024

(54) LACTIPLANTIBACILLUS PLANTARUM TCI837, METHODS FOR USING THE SAME, AND IRON SUPPLEMENT COMPOSITION HAVING THE SAME

(71) Applicant: TCI CO., LTD., Taipei (TW)

(72) Inventors: Yung-Hsiang Lin, Taipei (TW); Di Chang, Taipei (TW)

(73) Assignee: TCI CO., LTD., Taipei (TW)

( * ) Notice: Subject to any disclaimer, the term of this patent is extended or adjusted under 35 U.S.C. 154(b) by 38 days.

(21) Appl. No.: 17/564,250

(22) Filed: Dec. 29, 2021

(65) Prior Publication Data

US 2023/0210922 A1    Jul. 6, 2023

Related U.S. Application Data

(60) Provisional application No. 63/233,760, filed on Aug. 17, 2021.

(30) Foreign Application Priority Data

Nov. 30, 2021   (TW) ................. 110144719

(51) Int. Cl.
   *A61K 35/747*   (2015.01)
   *A61K 33/26*   (2006.01)
   *C12N 1/20*   (2006.01)

(52) U.S. Cl.
   CPC ............ *A61K 35/747* (2013.01); *A61K 33/26* (2013.01); *C12N 1/205* (2021.05)

(58) Field of Classification Search
   CPC ....... A61K 35/747; A61K 33/26; C12N 1/205
   See application file for complete search history.

(56) References Cited

U.S. PATENT DOCUMENTS 9,687,513 B2 *   6/2017   Alenfall ............... A61K 35/747

FOREIGN PATENT DOCUMENTS

CN    103642716 A    3/2014
CN    104207135 A    12/2014

OTHER PUBLICATIONS

Adiki, Shanta Kumari et al. "Enhancement in Iron Absorption on Intake of Chemometrically Optimized Ratio of Probiotic Strain Lactobacillus Plantarum 299v with Iron Supplement Pearl Millet." Biological trace element research 190.1 (2019): 150-156. Web. (Year: 2019).*
Zheng, Jinshui et al. "A Taxonomic Note on the Genus *Lactobacillus*: Description of 23 Novel Genera, Emended Description of the Genus *Lactobacillus* Beijerinck 1901, and Union of Lactobacillus and Leuconostocaceae." International journal of systematic and evolutionary microbiology 70.4 (2020): 27 (Year: 2020).*
Examination report dated Aug. 4, 2022, listed in correspondent Taiwan patent application No. 110144719.

* cited by examiner

*Primary Examiner* — Lora E Barnhart Driscoll
*Assistant Examiner* — Candice Lee Swift
(74) *Attorney, Agent, or Firm* — Chieh-Mei Wang

(57) ABSTRACT

Provided is a *Lactiplantibacillus plantarum* TCI837, deposited in the Leibniz Institute DSMZ under an accession number of DSM 33843. Based on this, the *Lactiplantibacillis plantarum* TCI837 can be used to prepare a composition for supplementing iron and/or promoting the absorption of iron in a subject, and to prepare a composition for improving the gut microbiota in a subject. In addition, the composition may be an iron supplement composition containing the *Lactiplantibacillus plantarum* TCI837 and an iron supplement.

6 Claims, 8 Drawing Sheets

Specification includes a Sequence Listing.

LACTIPLANTIBACILLUS PLANTARUM TCI837, METHODS FOR USING THE SAME, AND IRON SUPPLEMENT COMPOSITION HAVING THE SAME

CROSS-REFERENCES TO RELATED APPLICATIONS

This application claims the benefit of U.S. provisional application Ser. No. 63/233,760, filed on Aug. 17, 2021 and claims the priority of Patent Application No. 110144719 filed in Taiwan, R.O.C. on Nov. 30, 2021. The entirety of the above-mentioned patent applications are hereby incorporated by references herein and made a part of the specification.

REFERENCE OF AN ELECTRONIC SEQUENCE LISTING

The contents of the electronic sequence listing (P212350USI_ST25.txt; Size: 7.16 KB; and Date of Creation: Dec. 29, 2021) is herein incorporated by reference in its entirety.

BACKGROUND

Technical Field

The present invention relates to a *Lactiplantibacillus plantarum* and methods therefor, and in particular, to a *Lactiplantibacillus plantarum* TCI837, which can be used to prepare a composition that supplements iron, promotes the absorption of iron in a subject, and/or improves the gut microbiota in a subject.

Related Art

Iron, as an essential nutrient for the human body, mainly produces heme in the human body. Generally, the daily dietary iron intake can meet the needs of healthy men and menopausal women, but not the needs of menstruating women aged 15-49, pregnant women, adolescents, and infants who have bigger needs.

Research showed that it is difficult for people with iron deficiency to supplement their daily needs through dietary iron. Iron in common foods is mainly divided into heme iron and non-heme iron. Among them, the heme iron, while easily absorbed, is prone to raise concern about over-absorption of trimethylamine N-oxide (TMAO, an important biological indicator of the risk of cardiovascular diseases); on the other hand, the non-heme iron is not easily absorbed. Therefore, sufficient daily iron intake has become the most common issue for nutritional deficiency across the globe. According to statistics from the World Health Organization, iron deficiency is not only prevalent in developing countries, but also a public health problem in developed countries.

In addition, iron absorption by intestines in human is highly limited. It was found from studies that 80% of iron intake of the human body is oxidized in the gastrointestinal tract into $Fe^{3+}$, which is not easily absorbed, causing 65-95% of iron intake to be lost in the intestines.

SUMMARY

In view of this, a *Lactiplantibacillus plantarum* TCI837 is provided, which can be used to prepare a composition that supplements iron, promotes the absorption of iron in a subject, and/or improves the gut microbiota in a subject. IDC-al_Sub,AMD In some embodiments, a *Lactiplantibacillus plantarum* TCI837 is deposited in Leibniz Institute DSMZ-German Collection of Microorganisms and Cell Cultures (Address: Inhoffenstr, 7 B D-38124 Braunschweig), Germany, in accordance with the Budapest Treaty, on Feb. 25, 2021, under the accession number of DSM 33843. Access to the deposited material will be available, during pendency of the present patent application, to anyone determined by the Director to be entitled to access under 37 CFR 1.14 and 35 U.S.C. 122; and subject to paragraph (b) of 37 CFR 1,808, all restrictions imposed by the depositor on the availability to the public of the deposited material will be irrevocably removed upon the granting of the patent.

In some embodiments, a *Lactiplantibacillus plantarum* TCI837 is deposited at the Food Industry Research and Development Institute under the accession number of BCRC 911038.

In some embodiments, a *Lactiplantibacillus plantarum* TCI837 is used to prepare a composition that supplements iron and/or promotes the absorption of iron in a subject. The composition contains an effective amount of *Lactiplantibacillus plantarum* TCI837, and the *Lactiplantibacillus plantarum* TCI837 is deposited in Leibniz Institute DSMZ under the accession number of DSM 33843.

In some embodiments, a method for supplementing iron and/or promoting absorption of iron in a subject in need thereof includes administering to the subject a composition including an effective dose of *Lactiplantibacillus plantarum* TCI837 deposited in Leibniz Institute DSMZ under the accession number of DSM 33843.

In some embodiments, the composition is an iron supplement composition for supplementing iron.

In some embodiments, promoting absorption of iron in the subject in need thereof includes increasing the content of ferritin in the subject, reducing the total iron-binding capacity of serum in the subject, increasing the content of red blood cells in the subject, increasing the content of heme in the subject, increasing the hematocrit of the subject, or a combination thereof.

In some embodiments, when the subject is experiencing symptoms of iron-deficiency anemia, the *Lactiplantibacillus plantarum* TCI837 helps relieve the discomfort resulting from the iron-deficiency anemia.

In some embodiments, the symptoms of iron-deficiency anemia include cold hands and feet, cramps, hyposthenia, dizziness caused by changing postures, dizziness when calm, feeling of weakness, or a combination thereof.

In some embodiments, a *Lactiplantibacillus plantarum* TCI837 is used to prepare a composition that improves the gut microbiota in a subject. The composition contains an effective dose of *Lactiplantibacillus plantarum* TCI837 deposited in Leibniz Institute DSMZ under the accession number of DSM 33843. Improving the gut microbiota of the subject includes increasing probiotics and reducing non-probiotics.

In some embodiments, a method for improving gut microbiota in a subject in need thereof includes administering to the subject a composition including an effective dose of *Lactiplantibacillus plantarum* TCI837 deposited in Leibniz Institute DSMZ under the accession number of DSM 33843.

In some embodiments, bacteria in the gut microbiota include Enterobacteriaceae bacteria, *Campylobacter* bacteria, Intestinibacter bacteria, Lachnospiraceae NK4A136 group bacteria, and Lachnospiraceae [*Eubacterium*] *ruminantium* group bacteria.

In some embodiments, the *Lactiplantibacillus plantarum* TCI837 is acid-resistant, choline-resistant, and/or capable of colonizing the intestine of the subject.

In some embodiments, the composition inhibits the growth of the Enterobacteriaceae bacteria to delay the occurrence of an intestinal disease, and the intestinal disease includes intestinal inflammation, irritable bowel syndrome, or a combination thereof.

In some embodiments, the composition inhibits the growth of the *Campylobacter* bacteria to delay the occurrence of an intestinal disease, and the intestinal disease includes diarrhea, irritable bowel syndrome, or a combination thereof.

In some embodiments, the composition inhibits the growth of the Intestinibacter bacteria to ameliorate sleep disorders.

In some embodiments, the composition promotes the growth of the Lachnospiraceae NK4A136 group bacteria to produce butyric acid, thereby improving intestinal barrier functions of the subject.

In some embodiments, the composition promotes the growth of the Lachnospiraceae [*Eubacterium*] *ruminantium* group bacteria to decompose dietary fibers and produce butyric acid, thereby maintaining intestinal health of the subject.

In some embodiments, the composition has an effective dose of 50 mg/day of the *Lactiplantibacillus plantarum* TCI837.

In some embodiments, the composition further includes an effective dose of an iron supplement.

In some embodiments, an iron supplement composition is provided, including *Lactiplantibacillus plantarum* TCI837 and an iron supplement, wherein the *Lactiplantibacillus plantarum* TCI837 is deposited in Leibniz Institute DSMZ under an accession number of DSM 33843.

In some embodiments, the iron supplement is ferrous gluconate.

In some embodiments, a weight ratio of the *Lactiplantibacillus plantarum* TCI837 to the ferrous gluconate is 1:3.2.

In some embodiments, a content of the *Lactiplantibacillus plantarum* TCI837 is 50 mg, and a content of the ferrous gluconate is 160 mg.

In summary, *Lactiplantibacillus plantarum* TCI837 in any embodiment can be used to supplement iron, promote the absorption of iron in a subject, and/or improve the gut microbiota (such as promoting or inhibiting the growth of Enterobacteriaceae bacteria, *Campylobacter* bacteria, Intestinibacter bacteria, Lachnospiraceae NK4A 136 group bacteria, and Lachnospiraceae [*Eubacterium*] ruminantum group bacteria) of a subject. In some embodiments, the *Lactiplantibacillus plantarum* TCI837 can be used to prepare an iron supplement composition to supplement iron to increase the content of ferritin in the subject, reduce the total iron-binding capacity of serum in the subject, increase the content of red blood cells in the subject, increase the content of heme in the subject, increase the hematocrit of the subject, relieve the discomfort resulting from iron-deficiency anemia in the subject experiencing symptoms of iron-deficiency anemia (such as cold hands and feet, cramps, hyposthenia, dizziness caused by changing postures, dizziness when calm, and feeling of weakness), or a combination thereof. In some embodiments, *Lactiplantibacillus plantarum* TCI837 can be used to improve the gut microbiota in the subject and to increase probiotics and reduce non-probiotics to delay the occurrence of an intestinal disease (such as diarrhea, irritable bowel syndrome, and intestinal inflammation), ameliorate sleep disorders, improve intestinal barrier function of the subject, and maintain intestinal health of the subject. The *Lactiplantibacillus plantarum* TCI837 at a dose of 50 mg/day in any embodiment can help increase the iron absorption rate of a subject.

DETAILED DESCRIPTION

Figure 1:
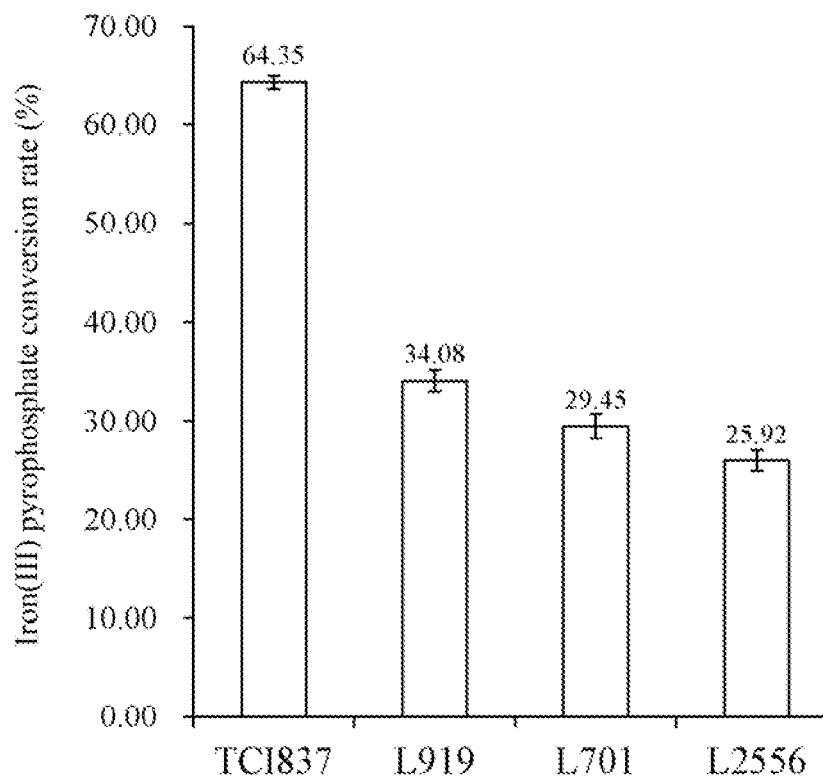
FIG. 1 is a graph showing an experimental result of an iron(III) pyrophosphate conversion rate of *Lactiplantibacillus plantarum* TCI837 and other *Lactiplantibacillus plantarum* strains.

*Lactiplantibacillus plantarum* TCI837 is a strain of *Lactobacillus* isolated from raisins. The *Lactiplantibacillus plantarum* TCI837 is deposited at the Leibniz Institute DSMZ-German Collection of Microorganisms and Cell Cultures (Address: Inhoffenstr. 7 B D-38124 Braunschweig), Germany, in accordance with the Budapest Treaty, on Feb. 25, 2021, under the accession number of DSM 33843, and deposited at the Food Industry Research and Development Institute under the accession number of BCRC 911038. In addition, the *Lactiplantibacillus plantarum* TCI837 can help supplement iron, promote the absorption of iron in a subject, and improve the gut microbiota in a subject. Promoting absorption of iron in the subject in need thereof includes increasing the content of ferritin in the subject, reducing the total iron-binding capacity of serum in the subject, increasing the content of red blood cells in the subject, increasing the content of heme in the subject, increasing the hematocrit of the subject, or a combination thereof. Improving the gut microbiota in the subject includes inhibiting the growth of non-probiotics and promoting the growth of probiotics. Herein, the subject is a human.

The *Lactiplantibacillus plantarum* TCI837 is Gram-negative bacteria, as well as anaerobic bacteria that can grow in an anaerobic environment. The *Lactiplantibacillus plantarum* TCI837 grows at 35-37° C., and can survive at pH 3-7.

In some embodiments, the *Lactiplantibacillus plantarum* TCI837 is resistant to gastric acid and bile salts. For example, using artificial gastric juice and artificial intestinal juice to simulate gastrointestinal environments, the *Lactiplantibacillus plantarum* TCI837 has a viability rate of 99.01% in the simulated gastric environment (pH 3-4) and has a viability rate of 97.90% in the simulated intestinal environment (pH 7-8). Therefore, the *Lactiplantibacillus plantarum* TCI837 is capable of colonizing the human gastrointestinal environment to help the host intestine absorb iron.

In some embodiments, the *Lactiplantibacillus plantarum* TCI837 can be used to supplement iron and/or promote absorption of iron in a subject to increase the content of ferritin in the subject, reduce the total iron-binding capacity of serum in the subject, increase the content of red blood cells in the subject, increase the content of heme in the subject, increase the hematocrit of the subject, or a combination thereof. In other words, the subject has the content of ferritin increased and utilization of iron transportation improved after taking the *Lactiplantibacillus plantarum* TCI837, which can make the subject have ruddy complexion and glowing looks.

In some embodiments, when the subject is experiencing symptoms of iron-deficiency anemia, the *Lactiplantibacillus plantarum* TCI837 helps relieve discomfort resulting from the iron-deficiency anemia. Specifically, taking the *Lactiplantibacillus plantarum* TCI837 can relieve the following symptoms of the subject: cold hands and feet, cramps, hyposthenia, dizziness caused by changing postures, dizziness when calm, and feeling of weakness.

In some embodiments, taking the *Lactiplantibacillus plantarum* TCI837 can improve the gut microbiota in a subject. For example, taking the *Lactiplantibacillus plantarum* TCI837 can inhibit the growth of Enterobacteriaceae bacteria, *Campylobacter* bacteria, and Intestinibacter bacteria in the intestine of the subject, and can promote the growth of Lachnospiraceae NK4A136 group bacteria and Lachnospiraceae [*Eubacterium*] *ruminantium* group bacteria in the intestine of the subject. In other words, taking the *Lactiplantibacillus plantarum* TCI837 can increase the content of probiotics and reduce the content of non-probiotics in the intestine of the subject. Herein, the non-probiotics include but not limit to Enterobacteriaceae bacteria, *Campylobacter* bacteria and Intestinibacter bacteria, and the probiotics include but not limit to Lachnospiraceae NK4A136 group bacteria, and Lachnospiraceae [*Eubacterium*] *ruminantium* group bacteria.

In addition, the growth of Enterobacteriaceae bacteria is inhibited to delay the occurrence of an intestinal disease such as diarrhea or irritable bowel syndrome. The growth of *Campylobacter* bacteria is inhibited to delay the occurrence of an intestinal disease such as diarrhea or irritable bowel syndrome. The growth of Intestinibacter bacteria is inhibited to ameliorate sleep disorders.

The growth of Lachnospiraceae NK4A136 group bacteria is promoted to produce butyric acid, and the growth of Lachnospiraceae [*Eubacterium*] *ruminantium* group bacteria is promoted to decompose dietary fibers and produce butyric acid, thereby improving intestinal barrier function of the subject and maintaining intestinal health of the subject.

In some embodiments, a supernatant of the *Lactiplantibacillus plantarum* TCI837 helps promote the intestine to absorb iron to increase the content of ferritin. In other words, taking the supernatant of the *Lactiplantibacillus plantarum* TCI837 or a composition prepared from the supernatant can promote the subject to absorb iron to relieve symptoms of iron-deficiency anemia and improve complexion of the subject. Herein, the term "supernatant" refers to a solution obtained by centrifuging a fermentation broth containing *Lactobacillus* to remove the bacterial precipitation, which includes metabolites of the *Lactobacillus*, but does not include the *Lactobacillus* itself. The term "metabolite" refers to a substance produced by metabolizing the *Lactobacillus* into a culture medium.

In some embodiments, a supernatant of the *Lactiplantibacillus plantarum* TCI837 can be collected after fermentation of the cultured *Lactiplantibacillus plantarum* TCI837. In some examples, the *Lactiplantibacillus plantarum* TCI837 is cultured in the BD Difco™ Lactobacilli MRS Broth in an anaerobic environment (that is, the oxygen concentration in the culture environment is 1 wt %) at 37° C. for 24 h, and then centrifuged at a rotational speed of 5,000×g for 20 min to separate the *Lactiplantibacillus plantarum* TCI837 strain, to obtain a supernatant of the fermented *Lactiplantibacillus plantarum* TCI837. Herein, the supernatant of the *Lactiplantibacillus plantarum* TCI837 includes metabolites of the *Lactiplantibacillus plantarum* TCI837, but may not include the *Lactiplantibacillus plantarum* TCI837 strain.

Based on this, in some embodiments, the *Lactiplantibacillus plantarum* T1837 and/or a supernatant thereof may be used to prepare a composition for promoting absorption of iron in a subject. In other words, taking the *Lactiplantibacillus plantarum* TCI837 and/or the supernatant thereof can supplement iron to relieve symptoms of iron-deficiency anemia and improve complexion of the subject. In some embodiments, the *Lactiplantibacillus plantarum* TCI837 can be used to prepare a composition for improving the gut microbiota in a subject. In other words, taking the composition containing the *Lactiplantibacillus plantarum* TCI837 can promote the growth of probiotics and inhibit the growth of non-probiotics in the intestine of the subject, thereby improving intestinal barrier functions, maintaining intestinal health, and delaying the occurrence of intestinal diseases.

In some embodiments, the foregoing composition may be a medicament. In other words, the medicament contains an effective content of *Lactiplantibacillus plantarum* TCI837 and/or supernatant thereof.

In some embodiments, the foregoing medicament may be manufactured into a dosage form suitable for enteral, parenteral, oral, or topical administration using techniques well known to those skilled in the art.

In some embodiments, the dosage form for enteral or oral administration includes, but is not limited to: a tablet, a troche, a lozenge, a pill, a capsule, a dispersible powder or granule, a solution, a suspension, an emulsion, a syrup, an elixir, a slurry, or other similar substances. For example, when the dosage form of a composition is a capsule, the composition contains $1 \times 10^9$ colony-forming unit/capsule (CFU/cap) of *Lactiplantibacillus plantarum* TCI837.

In some embodiments, the dosage form for parenteral or topical administration includes, but is not limited to: an injection, a sterile powder, an external preparation, or other similar substances. In some embodiments, the administration manner of the injection may be subcutaneous injection, intraepidermal injection, intradermal injection, or intralesional injection.

In some embodiments, the foregoing medicament may include a pharmaceutically acceptable carrier widely used in drug manufacturing technology. In some embodiments, the pharmaceutically acceptable carrier may be one or more of the following carriers: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, or other similar substances. The type and quantity of selected carriers fall within the scope of professionalism and routine technology of those skilled in the art. In some embodiments, the solvent of the pharmaceutically acceptable carrier may be water, normal saline, phosphate buffered saline (PBS), or aqueous solution containing alcohol.

In some embodiments, the foregoing composition may be a food. In other words, the food contains a specific content of *Lactiplantibacillus plantarum* TCI837. In some embodiments, the food may be an edible product or a food additive. In some embodiments, the edible product may be, but is not limited to: beverages, dairy products, fermented foods, bakery products, health foods, and dietary supplements.

In some embodiments, the foregoing composition may be a cosmeceutical or a cosmetic. In other words, the cosmeceutical or the cosmetic contains a specific content of *Lactiplantibacillus plantarum* TCI837 or supernatant thereof.

In some embodiments, the cosmeceutical or the cosmetic may be any one of the following types: toner, gel, jelly mask, mud mask, lotion, cream, lipstick, foundation, pressed powder, face powder, cleansing oil, cleansing milk, facial cleanser, body wash, shampoo, hair conditioner, sunscreen, hand cream, nail polish, perfume, essence, and facial mask.

In some embodiments, the cosmetic or the cosmeceutical may further contain acceptable ingredients for external products as required. In some embodiments, the acceptable ingredients for external products may be, for example, an emulsifier, a penetration enhancer, an emollient, a solvent, an excipient, an antioxidant, or a combination thereof.

In some embodiments, the foregoing composition has an effective dose of 50 mg/day of the *Lactiplantibacillus plantarum* TCI837. In some embodiments, the composition further includes an effective dose of iron supplement. The iron supplement may be, but is not limited to, ferrous gluconate. For example, the weight ratio of the *Lactiplantibacillus plantarum* TCI837 to the ferrous gluconate is 1:3.2. In an embodiment, the content of the *Lactiplantibacillus plantarum* TCI837 is 50 mg, and the content of the ferrous gluconate is 160 mg.

Numerical values used herein are approximate values, and all experimental data are expressed within the range of ±10%, and best within the range of ±5%.

Example 1: Strain Identification

Appropriate amounts of samples, taken from whole raisin, pu'er tea, black tomato peel, and Matsumoto mushroom respectively, were cultured in the BD Difco™ Lactobacilli MRS Broth in an anaerobic environment (that is, the oxygen concentration in the culture environment was 1 wt %) at 37° C. for 24 h to form different bacterial broths. Then, the bacterial broths were serially diluted before plated onto culture plates containing solid MRS medium (BD Difco™ Lactobacilli MRS Broth with 1.5% agar) respectively, and cultured in an anaerobic environment (that is, the oxygen concentration in the culture environment was 1 wt %) at 37° C., until single colonies are formed on each culture plate. A plurality of single colonies were picked from the solid MRS medium respectively to undergo strain identification by 16S rDNA sequencing of lactic acid bacteria. The polymerase chain reaction (PCR) was carried out to obtain 16S rDNA sequences (i.e., SEQ ID NO: 1 to SEQ ID NO: 4) of these single colonies. Then, by utilizing the National Center for Biotechnology Information (NCBI) website, the gene sequences as set forth in SEQ ID NO: 1 to SEQ ID NO: 4 were aligned with 16S rDNA sequences of other *Lactobacillus* strains, to obtain the similarity between the 16S rDNA sequences of these single colonies and the 16S rDNA sequences of other *Lactobacillus* strains, as shown in Table 1.

TABLE 1

| Strain NO. | Source of isolation | 16S rDNA sequence NO. | Similarity | *Lactobacillus* strain for alignment |
|---|---|---|---|---|
| TCI837 | Raisin | SEQ ID NO: 1 | 97.21-97.36% | *Lactiplantibacillus plantarum* (with subspecies Nos. MLG20-29, 8m-21, 70819, 6349, 7319, 6401, and 6093) |
| L919 | Pu'er tea | SEQ ID NO: 2 | 93.78-96.00% | *Lactiplantibacillus plantarum* (with subspecies Nos. SC12, CJH203, LY21, HDB1306, S6, IMAU70095, and M3) |
| L701 | Black tomato peel | SEQ ID NO: 3 | 98.65-98.74% | *Lactiplantibacillus plantarum* (with subspecies Nos. KPLP3, 7232, SN13T, Heal19, 2758, 2650, 2045, and 2034) |
| L2556 | Matsumoto mushroom | SEQ ID NO: 4 | 95.95-96.70% | *Lactiplantibacillus plantarum* (with subspecies Nos. 5955, CP2, NWAFU1539, 5642, 7031, S2-5-11, and 3596) |

It can be learned from the foregoing table that the 16S rDNA sequences of the four *Lactobacillus* strains are highly similar to those of other *Lactobacillus* strains, indicating that the four *Lactobacillus* strains are identified as *Lactiplantibacillus plantarum*.

The colony isolated from raisins and similar to other *Lactiplantibacillus plantarum* subspecies ("*Lactobacillus* strain for alignment" shown in Table 1) by 97.21%-97.36% was named *Lactiplantibacillus plantarum* TCI837. In addition, the *Lactiplantibacillus plantarum* TCI837 was deposited at the Leibniz Institute DSMZ (Address: Inhoffenstr. 7 B D-38124 Braunschweig), Germany, in accordance with the Budapest Treaty, on Feb. 25, 2021, under the accession number of DSM 33843, and deposited at the Food Industry Research and Development Institute under the accession number of BCRC 911038.

Example 2: Test of Iron (III) Pyrophosphate Conversion Rate of Different *Lactiplantibacillus plantarum* Strains The four strains (i.e., *Lactiplantibacillus plantarum* TCI837, *Lactiplantibacillus plantarum* L919, *Lactiplantibacillus plantarum* L701, and *Lactiplantibacillus plantarum* L2556) obtained in Example 1 were inoculated into the BD Difco™ Lactobacilli MRS Broth to culture in an anaerobic environment at 37° C. for 24 h to form various groups of to-be-tested bacterial broths. Then, 1 mL of the to-be-tested bacterial broth in each group was mixed with 3.6 µL of 10 mM ferric pyrophosphate citrate solution and 7 µL of 70 mM 3-(2-pyridyl)-5,6-diphenyl-1,2,4-triazine-p,p'-disulfonic acid monosodium salt hydrate (ferrozine, fz) aqueous solution to culture for 6 h, and then centrifuged to obtain a supernatant in each group for analysis.

A BD Difco™ Lactobacilli MRS Broth as a control group and the supernatants of each group were detected by ultraviolet-visible spectroscopy (UV-Vis) respectively to observe values at a wavelength of 562 nm indicating the formation of [FeII(fz)$_3$] complex and representing the capacity of the to-be-tested bacterial broth to reduce ferric iron to ferrous iron. In addition, as shown in FIG. 1, an iron (III) pyrophosphate conversion rate of *Lactiplantibacillus plantarum* in each group was calculated based on the values of the BD Difcom™ Lactobacilli MRS Broth measured at a wavelength of 562 nm.

Referring to FIG. 1, the iron (III) pyrophosphate conversion rate of *Lactiplantibacillus plantarum* TCI837 was 64.35%, the iron (I) pyrophosphate conversion rate of *Lactiplantibacillus plantarum* L919 was 34.08%, the iron (III) pyrophosphate conversion rate of *Lactiplantibacillus plantarum* L701 was 29.45%, and the iron (III) pyrophosphate conversion rate of *Lactiplantibacillus plantarum* L2556 was 25.92%. It can be learned that the iron (III) pyrophosphate conversion rate of *Lactiplantibacillus plantarum* TCI837 was 1.89 folds, 2.19 folds, 2.48 folds of those of other *Lactiplantibacillus plantarum* strains respectively. That is, the capacity of iron reduction of *Lactiplantibacillus plantarum* TCI837 was 1.9-2.5 folds of those of other *Lactiplantibacillus plantarum* strains.

Based on this, taking the *Lactiplantibacillus plantarum* TCI837 can help a subject reduce non-absorbable ferric iron obtained by oxidation in the gastrointestinal tract into ferrous iron in the intestine, thereby increasing the absorption rate of iron in the subject.

Example 3: Test of resistance to gastric acid and bile salts

Herein, the *Lactiplantibacillus plantarum* TCI837 obtained in Example 1 was tested in a buffer, an artificial gastric juice (pH 3), and an artificial intestinal juice (pH 7) each to determine the acid-base tolerance of the *Lactiplantibacillus plantarum* TCI837 in the gastrointestinal tract of organisms. The buffer was 0.2 M potassium chloride (KCl, Sigma-Aldrich) with pH of 7. The artificial gastric juice was 0.2 M KCl with pH of 3. The artificial intestinal juice was 0.2 M KCl and 0.3 wt % of bovine bile salts (Difco™ Oxgall) with pH of 7.

The *Lactiplantibacillus plantarum* TCI837 obtained in Example 1 was subjected to the following activation process as a target strain. In the activation process, 100 µL of frozen bacterial broth of the target strain was plated onto the solid MRS medium (BD Difco™ Lactobacilli MRS Broth with 1.5% agar) and cultured in an anaerobic environment (that is, the oxygen concentration in the culture environment was 1 wt %) at 37° C. for 16 h, to obtain single colonies of the target strain. Next, the single colonies of the target strain were picked into 15 mL of MRS medium (BD Difco™ Lactobacilli MRS Broth) and cultured in an anaerobic environment at 37° C. for 16 h, to obtain the activated target strain.

Then, 1 vol % of the activated target strain was inoculated into 20 mL of to-be-tested solution, and then shake cultured at a rotational speed of 50 rpm in an anaerobic environment at 37° C. for 3 h. The to-be-tested solutions in three groups were respectively an artificial gastric juice group, an artificial intestinal juice group, and a KCl buffer group (as a control group). 100 µL of cultured bacterial broth was taken to plate and then static cultured in an anaerobic environment at 37° C. for 3 days, and the number of viable bacteria in each group was counted by plate counting after 3 days.

Figure 2:
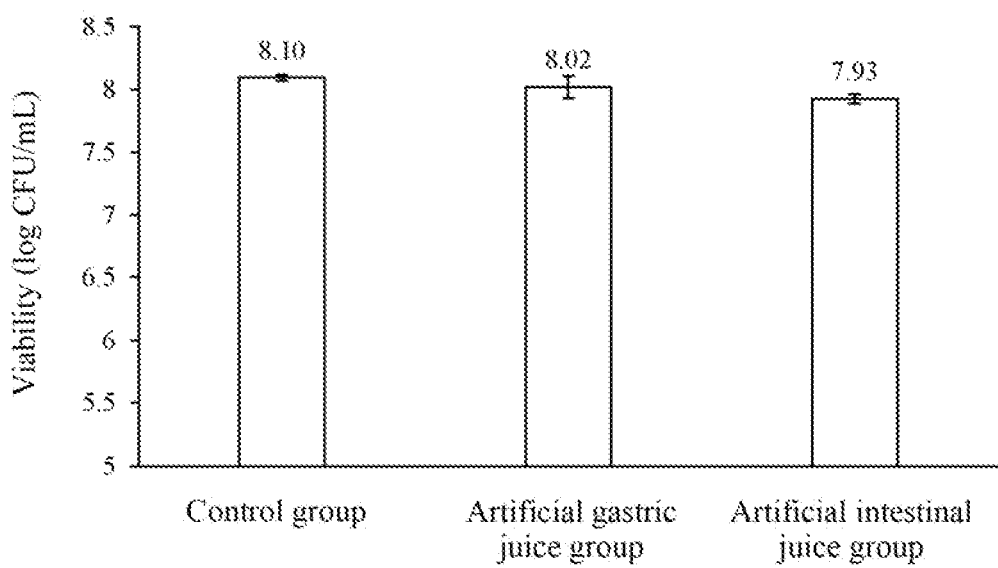
FIG. 2 is a graph showing an experimental result of viability of *Lactiplantibacillus plantarum* TCI837 in simulated gastrointestinal environments.

Referring to FIG. 2, the viability of *Lactiplantibacillus plantarum* TCI837 in the figure was expressed by the number of viable bacteria after counting in log CFU/mL. Log CFU/mL means the colony-forming unit (CFU) per milliliter of bacterial broth in logarithm (log). It can be learned from FIG. 2 that the viability of *Lactiplantibacillus plantarum* TCI837 in the control group was 8.10 log CFU/mL, the viability of *Lactiplantibacillus plantarum* TCI837 in the artificial gastric juice group was 8.02 log CFU/mL, and the viability of *Lactiplantibacillus plantarum* TCI837 in the artificial intestinal juice group was 7.93 log CFU/mL. That is, compared with the control group (regarded as having a viability rate of 100%), the viability rate of *Lactiplantibacillus plantarum* TCI837 in the artificial gastric juice group was 99.01%, and the viability rate of *Lactiplantibacillus plantarum* TCI837 in the artificial intestinal juice group was 97.90%.

Based on this, the *Lactiplantibacillus plantarum* TCI837 is resistant to gastric acid and bile salts, indicating that the *Lactiplantibacillus plantarum* TCI837 can resist the pH pressure from the host gastrointestinal tract to colonize the host intestine.

Example 4: Test of Intestinal Colonization

Herein, the colonization state of co-cultured intestinal epithelial cells (hereinafter referred to as Caco-2 cells, ATCC HTB-37TM) and *Lactiplantibacillus plantarum* TCI837 was observed by using a microscope, and the colonization rate thereof was analyzed by plate counting, to determine the colonization status of the *Lactiplantibacillus plantarum* TCI837 in the intestine. The intestine is the largest organ for digestion and absorption. Probiotics with a higher intestinal colonization rate can exert their effectiveness more efficiently.

First, the Caco-2 cells were inoculated into a six-well culture plate containing 2 mL of cell culture medium per well in a density of 7.5×10$^5$ cells per well, and then cultured in a thermostatic incubator at 37° C. with a carbon dioxide concentration of 5% for 24 h, to obtain a to-be-tested cell culture plate. Herein, the cell culture medium was prepared by adding 10% of fetal bovine serum (Gibco. Cat. 10438-026), 1% of penicillin/streptomycin (Gibco, Cat. 15140-122), and 0.01 mg/mL of human transferrin (Sigma) into the Dulbecco's Modified Eagle Medium (DMEM, Gibco, Cat. 12100-038).

Next, the *Lactiplantibacillus plantarum* TCI837 obtained in Example 1 was inoculated onto the MRS medium (BD Difco™ Lactobacilli MRS Broth) and cultured in a thermostatic incubator at 37° C. for 24 h. The $OD_{600}$ absorbance of the cultured bacterial broth (hereinafter referred to as activated bacterial broth) was measured by using an ELISA Reader, and the number of bacteria in the activated bacterial broth was calculated according to the ratio of $5 \times 10^8$ CFU per OD. Then, the activated bacterial broth was centrifuged to collect the pellet of *Lactiplantibacillus plantarum* TCI837 strain, the pellet of *Lactiplantibacillus plantarum* TCI837 strain was re-dissolved in a to-be-tested culture medium to form a to-be-tested bacterial broth, and the absorbance $OD_{600}$ of the to-be-tested bacterial broth was measured to result in a calculated concentration of 9.34 log CFU/mL. Herein, the to-be-tested culture medium was prepared by adding 10% of fetal bovine serum and 0.01 mg/mL of human transferrin into the DMEM (i.e., cell culture medium without 1% of penicillin/streptomycin).

The cell culture medium was removed from the to-be-tested cell culture plate and then the to-be-tested cell culture plate was washed with 1×PBS (Gibco), and 1 mL of to-be-tested bacterial broth was added into the to-be-tested cell culture plate washed with 1×PBS and then cultured in an anaerobic environment (that is, the oxygen content was below 1%) at 37° C. for 1 h, to obtain an analysis cell culture plate.

Next, the supernatant was removed from the analysis cell culture plate, and then the analysis cell culture plate was washed with 2 mL of 1×PBS for five times. Then, 1 mL of Triton X-100 (a nonionic surfactant) was added to each well of the washed analysis cell culture plate, and reacted at room temperature for 10 min to detach the Caco-2 cells and the *Lactiplantibacillus plantarum* TCI837 from the analysis cell culture plate to give an analysis broth. The analysis broth was plated on an agaropectin plate by dilution and spreading, the concentration of *Lactiplantibacillus plantarum* TCI837 in the analysis broth obtained by plate counting was 8.59 log CFU/mL, and the intestinal colonization rate of *Lactiplantibacillus plantarum* TCI837 was calculated, as shown in FIG. 3.

Figure 3:
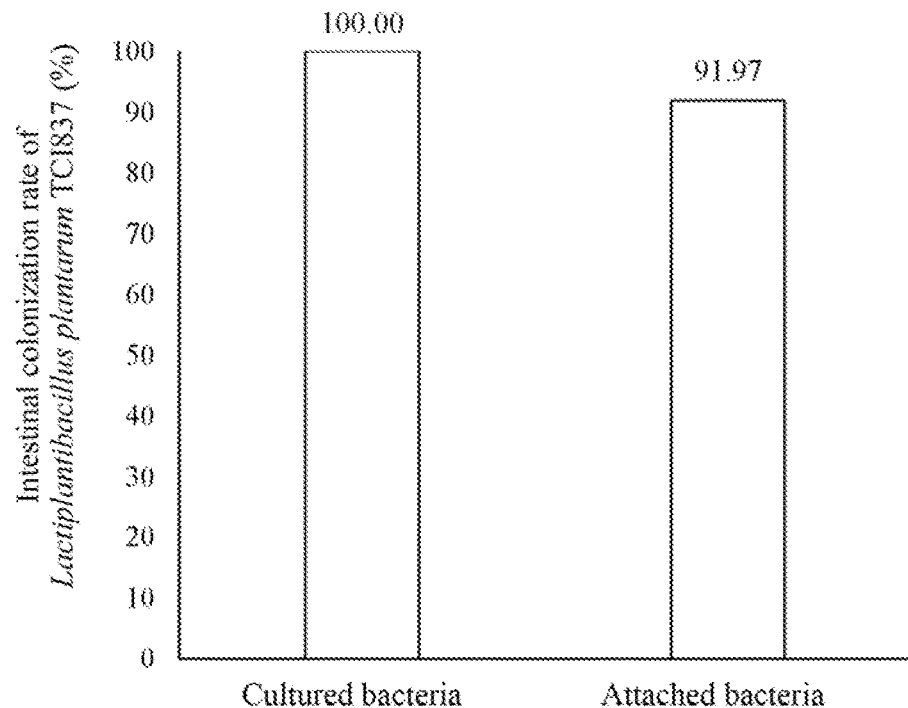
FIG. 3 is a graph showing an experimental result of an intestinal colonization rate of *Lactiplantibacillus plantarum* TCI837.

Referring to FIG. 3, the intestinal colonization rate of actually attached bacteria (that is, the analysis broth containing 8.59 log CFU/mL of *Lactiplantibacillus plantarum* TCI837) was 91.97% based on the intestinal colonization rate of cultured bacteria (that is, the to-be-tested bacterial broth containing 9.34 log CFU/mL of *Lactiplantibacillus plantarum* TCI837) regarded as 100%. That is, after 9.34 log CFU/mL of *Lactiplantibacillus plantarum* TCI837 was co-cultured with the Caco-2 cells, 8.59 log CFU/mL of *Lactiplantibacillus plantarum* TCI837 was attached to the Caco-2 cells. It can be learned that the intestinal colonization rate of *Lactiplantibacillus plantarum* TCI837 was at least 91.97%. In addition, the *Lactiplantibacillus plantarum* TCI837 can secrete mannose to improve its adhesion to the intestine and promote the intestinal epithelial cells to secrete mucin, and the binding of mucin and iron ions in the intestine can promote the absorption of iron ions. Based on this, the *Lactiplantibacillus plantarum* TCI837 promoted a subject to absorb iron for iron supplement.

Example 5: Preparation of Supernatant of *Lactiplantibacillus plantarum* TCI837

Herein, the culture medium used was the BD Difco™ Lactobacilli MRS Broth.

First, the *Lactiplantibacillus plantarum* TCI837 obtained in Example 1 was inoculated in the BD Difcom™ Lactobacilli MRS Broth to culture in a thermostatic incubator at 37° C. for 24 h, to obtain a *Lactiplantibacillus plantarum* TCI837 broth. The *Lactiplantibacillus plantarum* TCI837 broth was centrifuged at a rotational speed of 5,000×g for 20 min by using the Thermo Megafuge 16 centrifuge to separate the *Lactiplantibacillus plantarum* TCI837 strain, to obtain a supernatant of the fermented *Lactiplantibacillus plantarum* TCI837.

Therefore, the supernatant of the *Lactiplantibacillus plantarum* TCI837 containing metabolites of the *Lactiplantibacillus plantarum* TCI837 can be obtained.

Example 6: Test of Absorption of Iron in Intestine

Ferritin can be used as an indicator of iron content in the body. Herein, the measurement of ferritin can be used as a criterion for absorption of iron in intestinal cells.

The cells used were intestinal epithelial cells (hereinafter referred to as Caco-2 cells, ATCC HTB-37TM). The cell culture medium used was prepared by adding 20% of fetal bovine serum (Gibco, Cat. 10438-026) and 1% of antibiotic-antimycotic (Gibco, Cat. 15140-122) into the Dulbecco's Modified Eagle Medium (DMEM, Gibco, Cat. 12100-038). The iron-free culture medium used was prepared by adding 10 mmol/L of PIPES (Thermo), 4 mg/L of hydrocortisone (Thermo), 5 µg/L of sodium selenite (Thermo), 34 µg/L of triiodothyronine (Thermo), 5 mg/L of insulin (Thermo), 20 µg/L of epidermal growth factor (Thermo), and 1% of antibiotic-antimycotic into a minimum essential medium (Gibco).

The Caco-2 cells were inoculated into a 24-well culture plate containing 500 µL of cell culture medium per well at a density of $2.0 \times 10^4$ cells per well, and then cultured in a thermostatic incubator at 37° C. with a carbon dioxide concentration of 5% for 14 days, the cell culture medium was changed every three days, and the test of absorption of iron was carried out after the 14 days of culture.

The cell culture medium was removed from the 24-well culture plate 2 days before the test of absorption of iron, and replaced with the iron-free culture medium for culturing after the 24-well culture plate was washed with 1×PBS (available from Gibco).

Groups were divided into a control group and an experimental group. After replacement to the iron-free culture medium, after 2 days of culture, the iron-free culture medium in the 24-well culture plate was replaced with an experimental culture medium. Herein, the experimental culture medium in the experimental group was an iron-free culture medium containing 0.125% of the supernatant of the *Lactiplantibacillus plantarum* TCI837 prepared in Example 5, and the experimental culture medium in the control group was an iron-free culture medium containing 0.1 µmol/mL of ascorbic acid (Sigma). Next, 0.1% of ferrous gluconate was added into the two groups as an iron source, and then cultured in a thermostatic incubator at 37° C. with a carbon dioxide concentration of 5% for 24 h.

Figure 4:
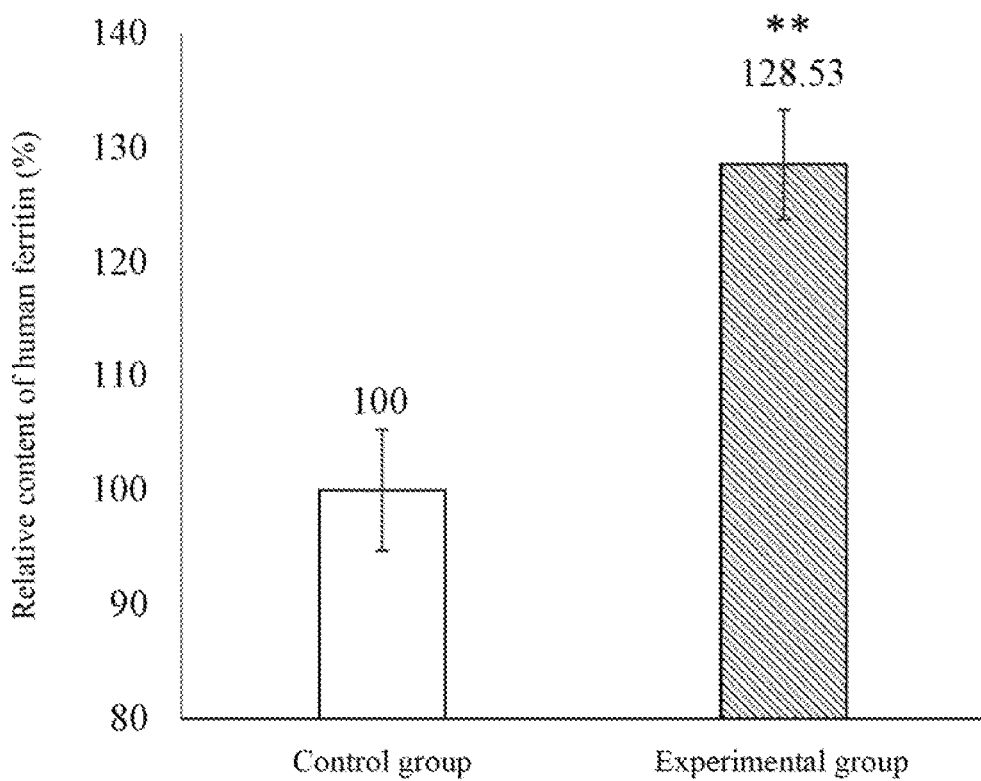
FIG. 4 is a graph showing an experimental result of a ferritin content of intestinal cells.

Then, the Caco-2 cells of the two groups were collected with 200 µL of RIPA buffer (Thermo) to obtain a cell solution, the concentration of protein in the cell solution was measured by Bradford protein assay, and the content of human ferritin in the cell solution was measured by using the Human Ferritin (FTL) ELISA kit (Abcam). The content of human ferritin measured in the control group was regarded as 100%. As shown in FIG. 4, it is to be noted that the statistically significant difference between the groups was determined by student's t-test. Moreover, in FIG. 4, "**" represents a p value less than 0.05 in comparison with the control group.

Referring to FIG. 4, compared with the control group, the content of human ferritin in the experimental group was 128.53%. It can be learned that the content of human ferritin in the experimental group was significantly increased, indicating that the Caco-2 cells treated with the supernatant of the *Lactiplantibacillus plantarum* TCI837 for 24 h can produce more human ferritin as an indicator of human iron storage. It can be learned that the supernatant of the *Lactiplantibacillus plantarum* TCI837 helped promote intestinal cells to absorb iron and produce ferritin.

Based on this, the *Lactiplantibacillus plantarum* TCI837 and/or the supernatant thereof can help promote intestinal cells to absorb iron and produce ferritin. After a subject takes the *Lactiplantibacillus plantarum* TCI837, the *Lactiplantibacillus plantarum* TCI837 that colonizes in the body can help promote intestinal cells to absorb iron ions and produce ferritin, thereby increasing the content of iron in the body for iron supplement.

Example 7: Human Subject Experiment

To further determine the effect of *Lactiplantibacillus plantarum* TCI837 on the human body, seven subjects were classified into a control group and an experimental group. In the control group, three subjects were provided with capsules containing 160 mg of ferrous gluconate (from Zhengzhou Ruipu) (with 20 mg of iron therein) each. In the experimental group, four subjects were provided with capsules containing 160 mg of ferrous gluconate (from Zhengzhou Ruipu) (with 20 mg of iron therein) and 50 mg of *Lactiplantibacillus plantarum* TCI837 ($4\times10^{11}$ CFU) each. The seven subjects took one capsule every morning before meals for four weeks.

The seven subjects were those with "anemia symptoms" or low heme value (<11.5 μm/dL) as determined by health check.

Example 7-1: Blood Test

Each of the seven subjects was subjected to blood test (entrusted to LEZEN Lab.) by respectively drawing 6 mL of venous blood before taking the capsule (week 0), after taking the capsule for 2 weeks (week 2), and after taking the capsule for 4 weeks (week 4) by using a purple-top blood collection tube containing EDTA as an anticoagulant. The test items included the content of ferritin in the blood of the subject, the total iron-binding capacity (TIBC) of serum in the subject, the content of red blood cells in the blood of the subject, the content of heme in the blood of the subject, and the hematocrit (HCT) of the subject. In addition, the four subjects in the experimental group were asked to fill in a questionnaire on the severity of symptoms of iron-deficiency anemia before taking the capsule (week 0) and after taking the capsule for 2 weeks (week 2) to determine whether the *Lactiplantibacillus plantarum* TCI837 can relieve the discomfort caused by iron-deficiency anemia.

Figure 5:
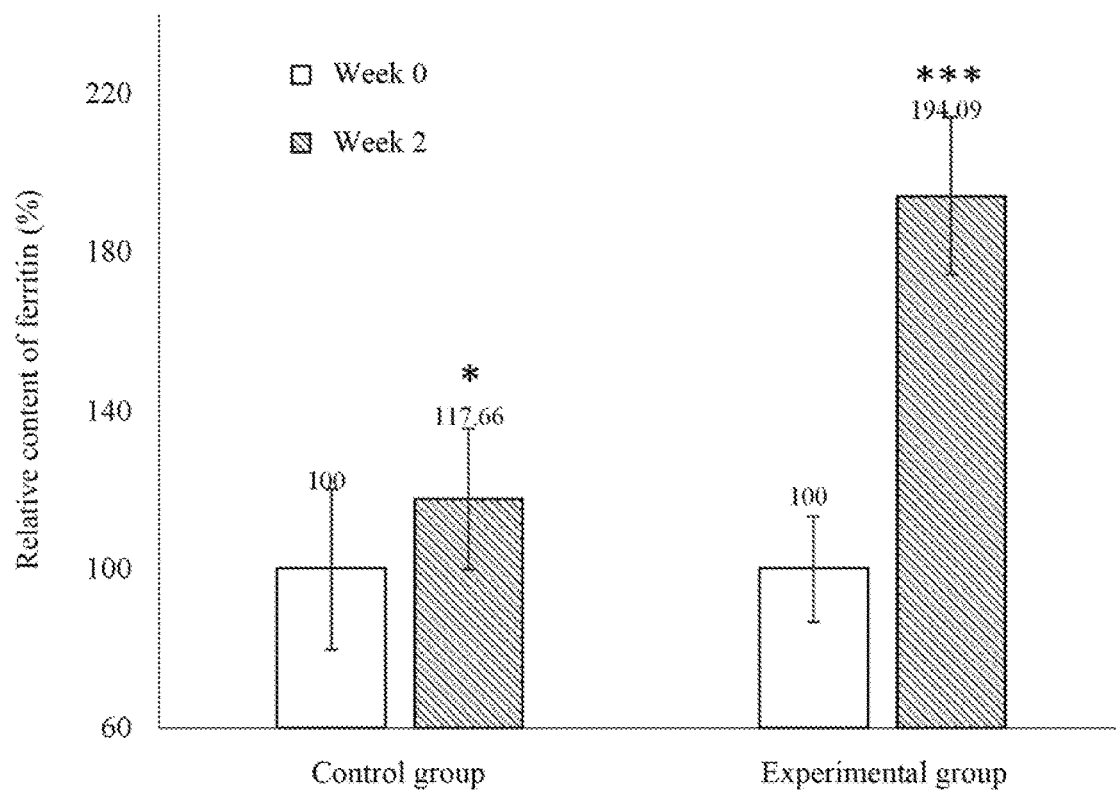
FIG. 5 is an analysis graph of a human subject experiment of a ferritin content in blood at week 0 and week 2.

Referring to FIG. 5, the average content of ferritin in the blood of the subjects in the experimental group and the control group at week 2 was calculated based on the average content of ferritin in the blood of the subjects at week 0 regarded as 100%. In addition, ferritin is one of the indicators that reflect the amount of iron in the body, and it is also a gold indicator for the diagnosis of iron-deficiency anemia. It can be learned from FIG. 5 that the average content of ferritin in the blood of the subjects in the control group was 117.66%. and the average content of ferritin in the blood of the subjects in the experimental group was 194.09%. That is, the content of ferritin of the experimental group at week 2 was 1.94 folds of that at week 0, which was much higher than the 1.18 folds of increase of the control group.

In other words, after taking one capsule containing the *Lactiplantibacillus plantarum* TCI837 and iron supplement (ferrous gluconate) every morning before meals for 2 weeks, the subjects in the experimental group have the increase of the average content of ferritin at least about 1.7 folds of that of the control group.

It can be learned that, compared with only taking an iron supplement, taking a composition containing the *Lactiplantibacillus plantarum* TCI837 and iron supplement can significantly increase the content of ferritin in the subject, indicating that the *Lactiplantibacillus plantarum* TCI837 can effectively help the subject to absorb iron and significantly help the subject to supplement iron.

Figure 6:
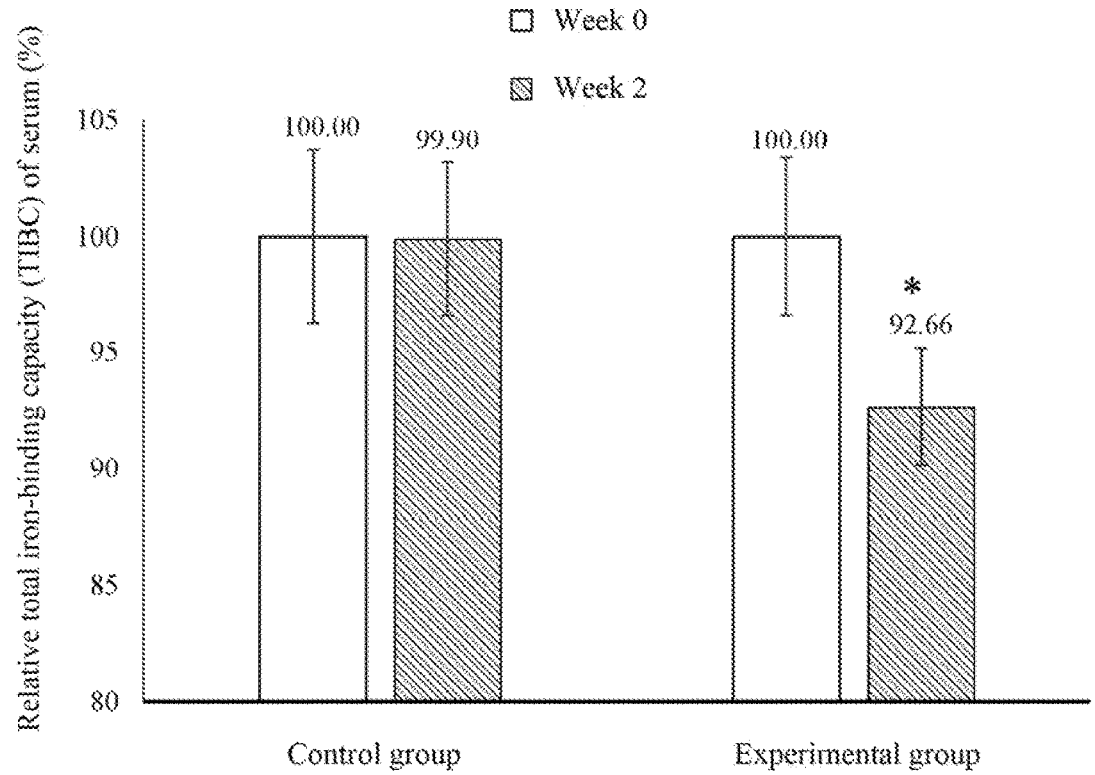
FIG. 6 is an analysis graph of a human subject experiment of a total iron-binding capacity (TIBC) of serum at week 0 and week 2.

Referring to FIG. 6, the average total iron-binding capacity (TIBC) of serum in the subjects in the experimental group and the control group at week 2 was calculated based on the average total iron-binding capacity of serum in the subjects at week 0 regarded as 100%. The total iron-binding capacity of serum represents the unsaturated iron-binding capacity (UIBC). A high total iron-binding capacity of serum represents that the body is deficient in iron, and a low total iron-binding capacity of serum represents that the iron transport and utilization efficiency is improved. It can be learned from FIG. 6 that the average total iron-binding capacity of serum of the subjects in the control group was 99.9%, and the average total iron-binding capacity of serum of the subjects in the experimental group was 92.66%. That is, the average total iron-binding capacity of serum of the experimental group at week 2 was 0.927 folds of that at week 0, which was much lower than the 0.999 folds of decrease of the control group.

In other words, the subjects in the experimental group after taking one capsule containing the *Lactiplantibacillus plantarum* TCI837 and iron supplement (ferrous gluconate) every morning before meals for 2 weeks have the transferrin efficiency increased by 7.3%.

It can be learned that, compared with only taking an iron supplement, taking a composition containing the *Lactiplantibacillus plantarum* TCI837 and iron supplement significantly increased the transferrin efficiency of the subject, indicating that the *Lactiplantibacillus plantarum* TCI837 effectively helped the subject to absorb iron and significantly help the subject to supplement iron.

Figure 7:
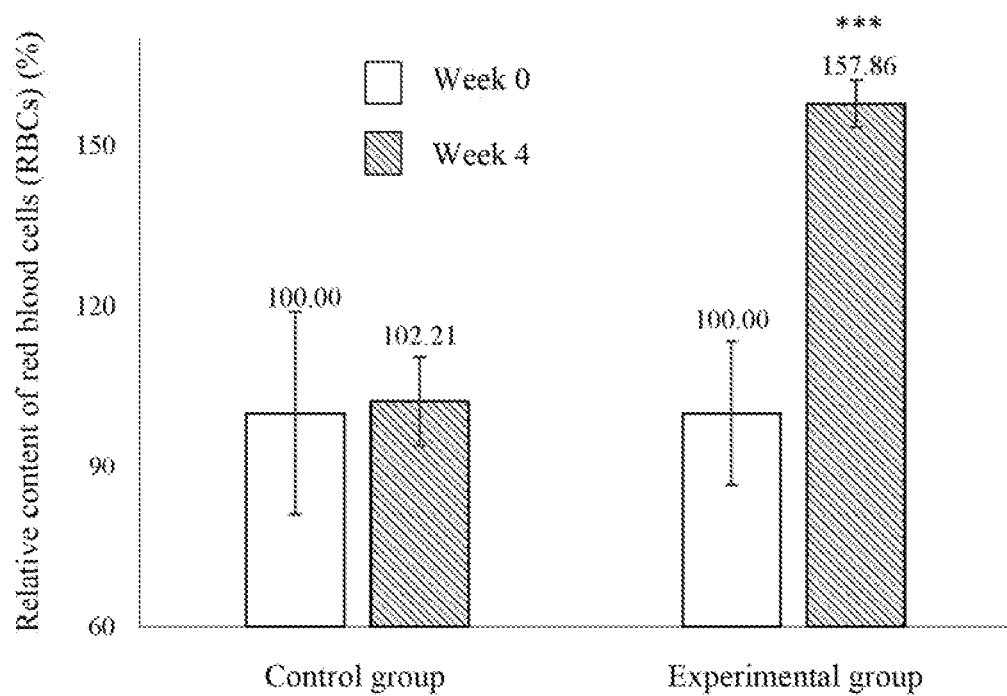
FIG. 7 is an analysis graph of a human subject experiment of a red blood cell (RBC) content at week 0 and week 4.

Referring to FIG. 7, the average content of red blood cells (RBCs) of the subjects in the experimental group and the control group at week 4 was calculated based on the average content of red blood cells of the subjects at week 0 regarded as 100%. It can be learned from FIG. 7 that the average content of red blood cells of the subjects in the control group was 102.21%, and the average content of red blood cells of the subjects in the experimental group was 157.86%. That is, the average content of red blood cells of the experimental group at week 4 was 1.58 folds of that at week 0, which was much higher than the 1.02 folds of increase of the control group.

In other words, the subjects in the experimental group after taking one capsule containing the *Lactiplantibacillus plantarum* TCI837 and iron supplement (ferrous gluconate) every morning before meals for 1 month had the content of red blood cells increased by 58%.

It can be learned that, compared with only taking an iron supplement, taking a composition containing the *Lactiplantibacillus plantarum* TCI837 and iron supplement significantly increased the content of red blood cells of the subject, indicating that the *Lactiplantibacillus plantarum* TCI837 effectively helped the subject to absorb and supplement iron, thereby increasing the content of red blood cells of the subject and making the subject have ruddy complexion and glowing looks.

Figure 8:
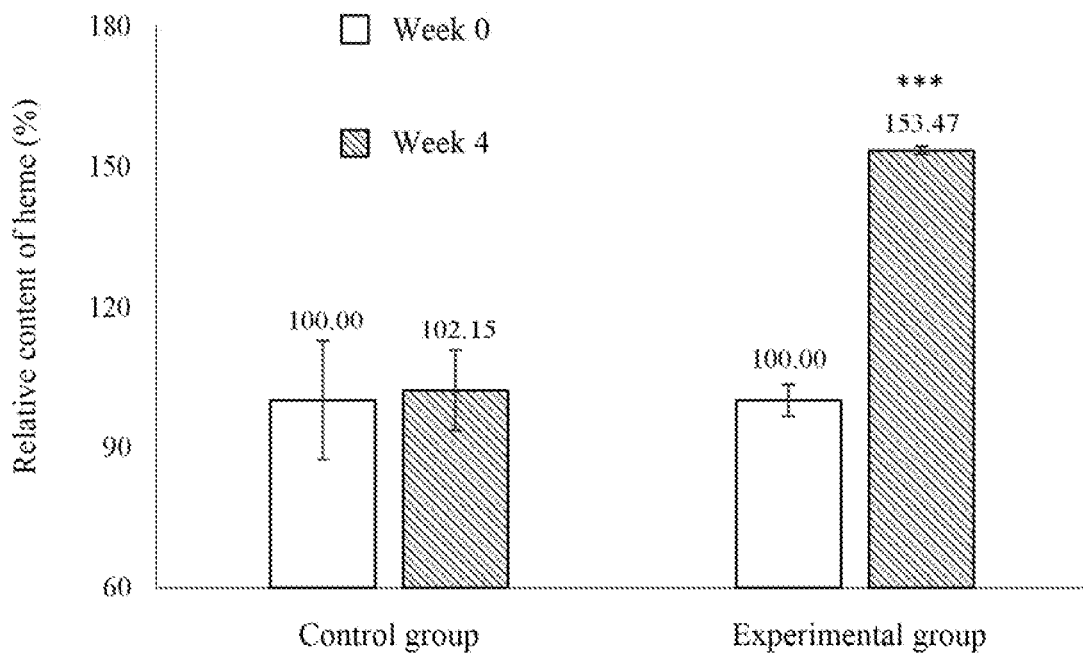
FIG. 8 is an analysis graph of a human subject experiment of a heme content at week 0 and week 4.

Referring to FIG. 8, the average content of heme of the subjects in the experimental group and the control group at week 4 was calculated based on the average content of heme of the subjects at week 0 regarded as 100%. It can be learned from FIG. 8 that the average content of heme of the subjects in the control group was 102.15%, and the average content of heme of the subjects in the experimental group was 153.47%. That is, the average content of heme of the experimental group at week 4 was 1.54 folds of that at week 0, which was much higher than the 1.02 folds of increase of the control group.

In other words, the subjects in the experimental group after taking one capsule containing the *Lactiplantibacillus plantarum* TCI837 and iron supplement (ferrous gluconate) every morning before meals for 1 month had the content of heme increased by 53%.

It can be learned that, compared with only taking an iron supplement, taking a composition containing the *Lactiplantibacillus plantarum* TCI837 and iron supplement significantly increased the content of heme of the subject, indicating that the *Lactiplantibacillus plantarum* TCI837 effectively helped the subject to absorb and supplement iron, thereby increasing the content of heme of the subject and making the subject have ruddy complexion and glowing looks.

Figure 9:
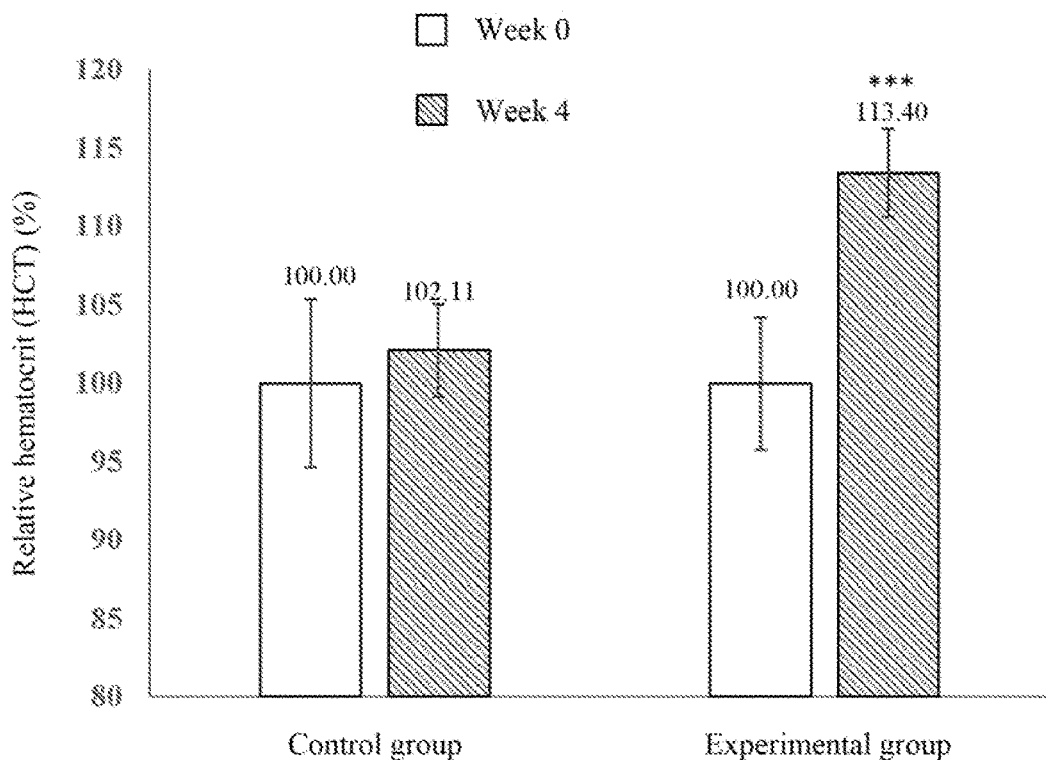
FIG. 9 is an analysis graph of a human subject experiment of a hematocrit (HCT) at week 0 and week 4.

Referring to FIG. 9, the average hematocrit (HCT) of the subjects in the experimental group and the control group at week 4 was calculated based on the average hematocrit of the subjects at week 0 regarded as 100%. It can be learned from FIG. 9 that the average hematocrit of the subjects in the control group was 102.11%, and the average hematocrit of the subjects in the experimental group was 113.40%. That is, the average hematocrit of the experimental group at week 4 was 1.13 folds of that at week 0, which was much higher than the 1.02 folds of increase of the control group.

In other words, the subjects in the experimental group after taking one capsule containing the *Lactiplantibacillus plantarum* TCI837 and iron supplement (ferrous gluconate) every morning before meals for 1 month had the hematocrit increased by 13%, indicating that the average volume of red blood cells in the blood was significantly increased by 13%.

It can be learned that, compared with only taking an iron supplement, taking a composition containing the *Lactiplantibacillus plantarum* TCI837 and iron supplement significantly increased the average volume of red blood cells in the blood of the subject, indicating that the *Lactiplantibacillus plantarum* TCI837 effectively helped the subject to absorb and supplement iron, thereby increasing the average volume of red blood cells of the subject and making the subject have ruddy complexion and glowing looks.

Example 7-2: Questionnaire

Herein, as shown in Table 2, the questionnaire items for analysis included: cold hands and feet, cramps, hyposthenia, dizziness caused by changing postures, dizziness when calm, and feeling of weakness.

TABLE 2

Comprehensive evaluation of severity of symptoms of iron-deficiency anemia

| | Option | | | | |
|---|---|---|---|---|---|
| Symptom | None (1) | Mild (2) | Obvious (3) | Serious (4) | Very serious (5) |
| Cold hands and feet | | | | | |
| Cramps | | | | | |
| Hyposthenia | | | | | |
| Dizziness caused by changing postures | | | | | |
| Dizziness when calm | | | | | |
| Feeling of weakness | | | | | |

In Table 2, "none" represents 1 point, "mild" represents 2 points, "obvious" represents 3 points, "serious" represents 4 points, and "very serious" represents 5 points. The severity of each test item was analyzed by adding up the scores.

Figure 10:
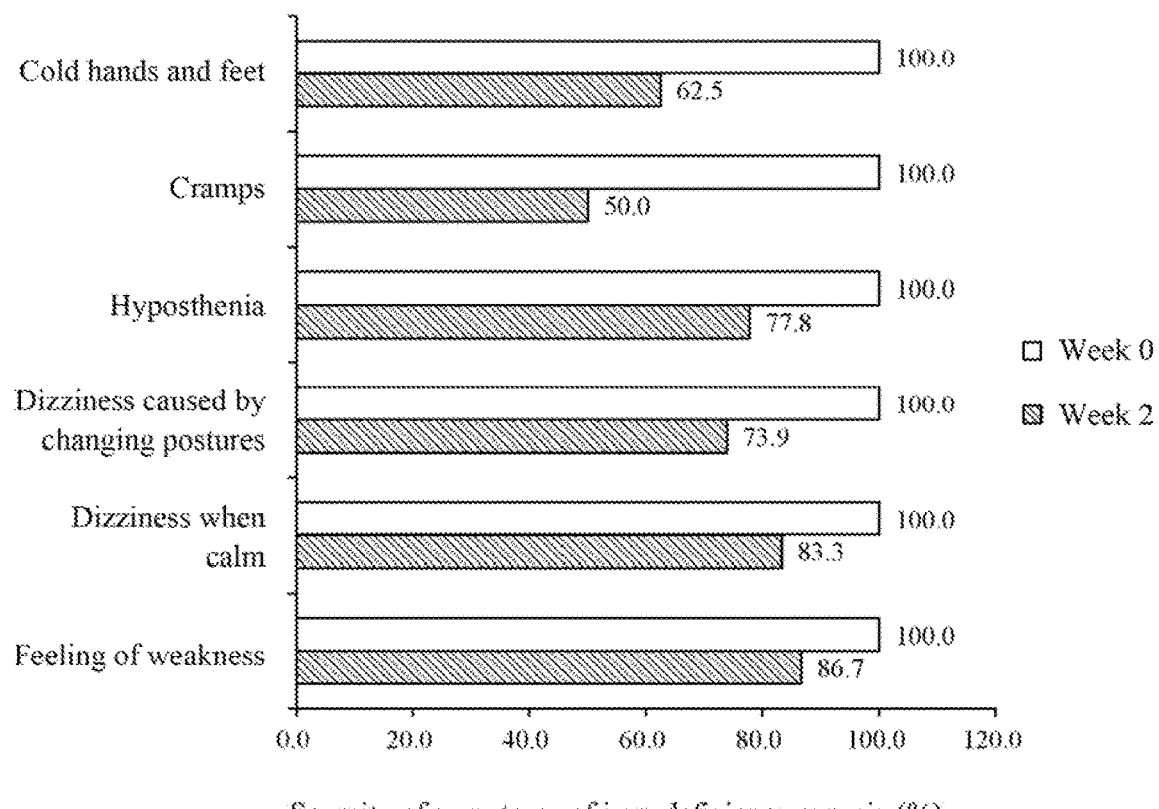
FIG. 10 is a graph showing a questionnaire result of severity of symptoms of iron-deficiency anemia at week 0 and week 2.

Referring to FIG. 10, the severity score percentage of the subjects in the experimental group at week 2 was calculated based on the severity score percentage of the subjects at week 0 regarded as 100%. It can be learned from FIG. 10 that, after taking one capsule containing the *Lactiplantibacillus plantarum* TCI837 and iron supplement (ferrous gluconate) every morning before meals for 2 weeks, the subjects in the experimental group had the severity score percentage of "cold hands and feet" decreased to 62.5%, the severity score percentage of "cramps" decreased to 50.0%, the severity score percentage of "hyposthenia" decreased to 77.8%, the severity score percentage of "dizziness caused by changing postures" decreased to 73.9%, the severity score percentage of "dizziness when calm" decreased to 83.3%, and the severity score percentage of "feeling of weakness" decreased to 86.7%.

It can be learned that taking a composition containing the *Lactiplantibacillus plantarum* TCI837 and iron supplement can significantly reduce the severity of various symptoms of iron-deficiency anemia.

Example 7-3: Test of Gut Microbiota

Herein, each of the seven subjects in the experimental group and the control group was subjected to stool sampling before taking the capsule (week 0) and after taking the capsule for 4 weeks (week 4) for analysis by BIOTOOLS. The analysis method is using metagenomeSeq as a species statistics method to detect significant differences in microbial colonies between groups, and carrying out multiple hypothesis testing and false discovery rate (FDR) analysis to evaluate the observed significant differences. In addition, the hypothesis testing is carried out based on the data of species abundances between groups to obtain a p value, the p value was corrected to obtain a corrected q value, and species were screened for significant differences according to the p value or q value. Moreover, the analysis of significant differences in species between groups is carried out at six levels, phyla, class, order, family, genus, and species, to obtain species with significant differences between two groups at different levels, thereby further drawing box plots of relative abundance distribution of species with differences between groups at each level, as shown in FIG. 11 to FIG. 15.

The species obtained from the stool samples of the seven subjects were Enterobacteriaceae bacteria, *Campylobacter* bacteria, Intestinibacter bacteria, Lachnospiraceae NK4A136 group bacteria, and Lachnospiraceae [*Eubacterium*]*ruminantium* group bacteria. The abundance of the Enterobacteriaceae bacteria was positively correlated with intestinal inflammation and irritable bowel syndrome; the abundance of the (*Campylobacter* bacteria was positively correlated with intestinal diseases such as diarrhea and irritable bowel syndrome; the abundance of the Intestinibacter bacteria was positively correlated with sleep disorders; the abundance of the Lachnospiraceae NK4A136 group bacteria that can produce butyric acid was positively correlated with intestinal barrier functions; and the Lachnospiraceae [*Eubacterium*] *ruminantium* group bacteria can decompose dietary fibers and produce butyric acid, thereby maintaining intestinal health.

Figure 11:
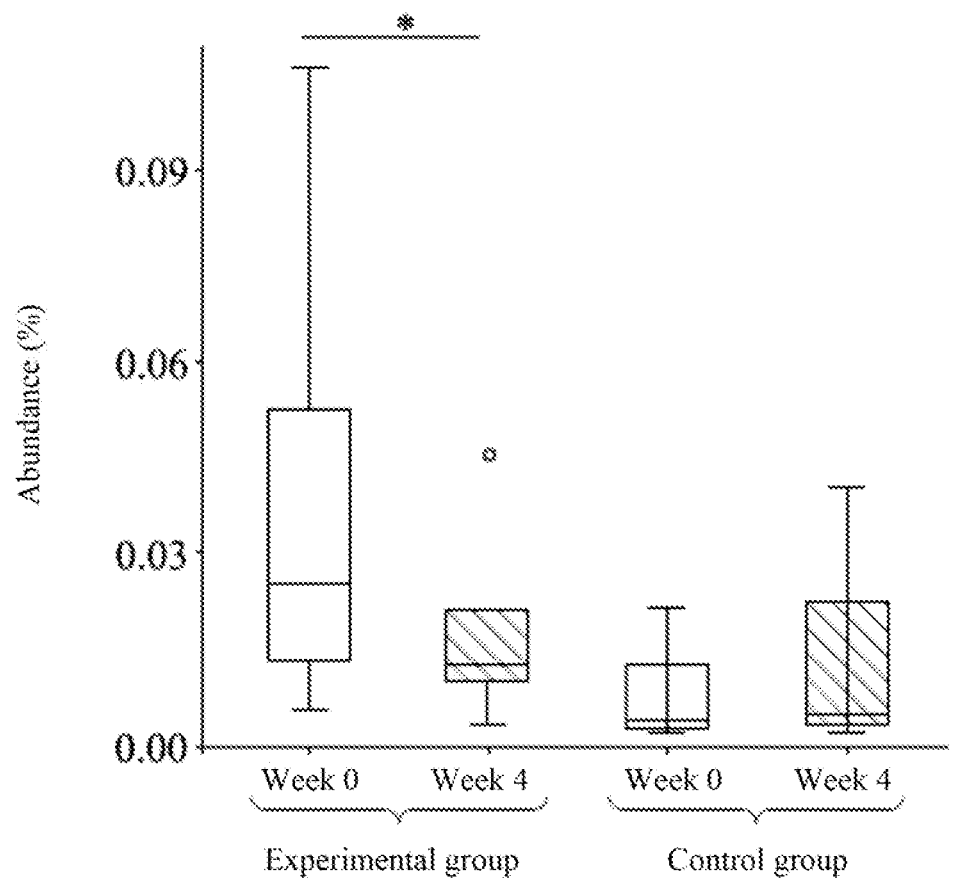
FIG. 11 is a graph showing an analysis result of abundance of Enterobacteriaceae bacteria at week 0 and week 4.

Referring to FIG. 11, in the experimental group at week 0, the four subjects had the abundances of the Enterobacteriaceae bacteria between 0.01% and 0.06% with an average abundance of 0.041% and an abundance median of 0.025%; in the control group at week 0, the three subjects had the abundances of the Enterobacteriaceae bacteria between 0.00% and 0.015% with an average abundance of 0.009% and an abundance median of 0.004%. The seven subjects after 4 weeks of taking the capsules for each group had different changes in gut microbiota. In the experimental group at week 4, the four subjects had the abundances of the Enterobacteriaceas bacteria between 0.005% and 0.025% with an average abundance of 0.019% and an abundance median of 0.013%; in the control group at week 4, the three subjects had the abundances of the Enterobacteriaceae bacteria between 0.00% and 0.025% with an average abundance of 0.016% and an abundance median of 0.005%.

It can be learned that the subjects to whom the composition containing the *Lactiplantibacillus plantarum* TCI837 and iron supplement was administered for 4 weeks in the experimental group had the average abundance of the Enterobacteriaceae bacteria reduced by 0.022%, and the subjects to whom only the iron supplement was administered for 4 weeks in the control group had the average abundance of the Enterobacteriaceae bacteria increased by 0.007%, indicating that the iron supplement with *Lactiplantibacillus plantarum* TCI837 helped significantly reduce the Enterobacteriaceae bacteria that tends to increase due to iron intake, thereby reducing the possibility of intestinal inflammation and irritable bowel syndrome.

Figure 12:
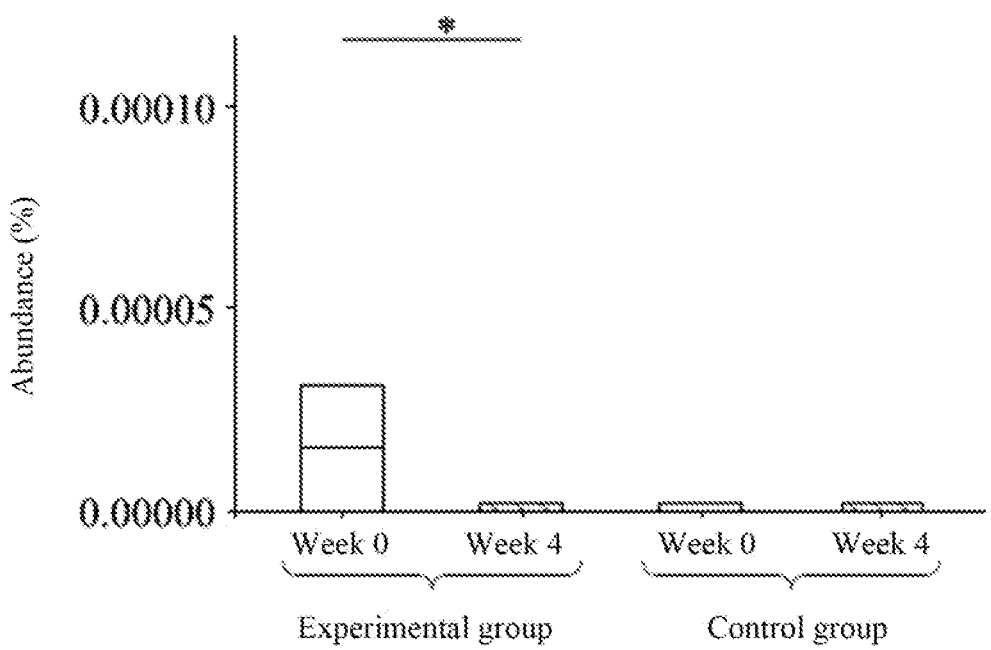
FIG. 12 is a graph showing an analysis result of abundance of *Campylobacter* bacteria at week 0 and week 4.

Referring to FIG. 12, in the experimental group at week 0, the four subjects had the abundances of the *Campylobacter* bacteria between 0.00% and $4\times10^{-5}$% with an average abundance of $1.51\times10^{-5}$% and an abundance median of $1.51\times10^{-5}$%; in the control group at week 0, the three subjects had the abundances of the *Campylobacter* bacteria around 0.00% with an average abundance of 0.00% and an abundance median of 0.00%. The seven subjects after 4 weeks of taking the capsules for each group had different changes in gut microbiota. In the experimental group at week 4, the four subjects had the abundances of the *Campylobacter* bacteria around 0.00% with an average abundance of $1.51\times10^{-5}$% and an abundance median of 0.00%; in the control group at week 4, the three subjects had the abundances of the *Campylobacter* bacteria around 0.00% with an average abundance of 0.00% and an abundance median of 0.00%.

It can be learned that the subjects to whom the composition containing the *Lactiplantibacillus plantarum* TCI837 and iron supplement was administered for 4 weeks in the experimental group had the abundance median of the *Campylobacter* bacteria reduced to 0.00%, indicating that most subjects in the experimental group reduced the *Campylobacter* bacteria in the intestine by taking the composition containing the *Lactiplantibacillus plantarum* TCI837 and iron supplement, thereby reducing the possibility of diarrhea and irritable bowel syndrome.

Figure 13:
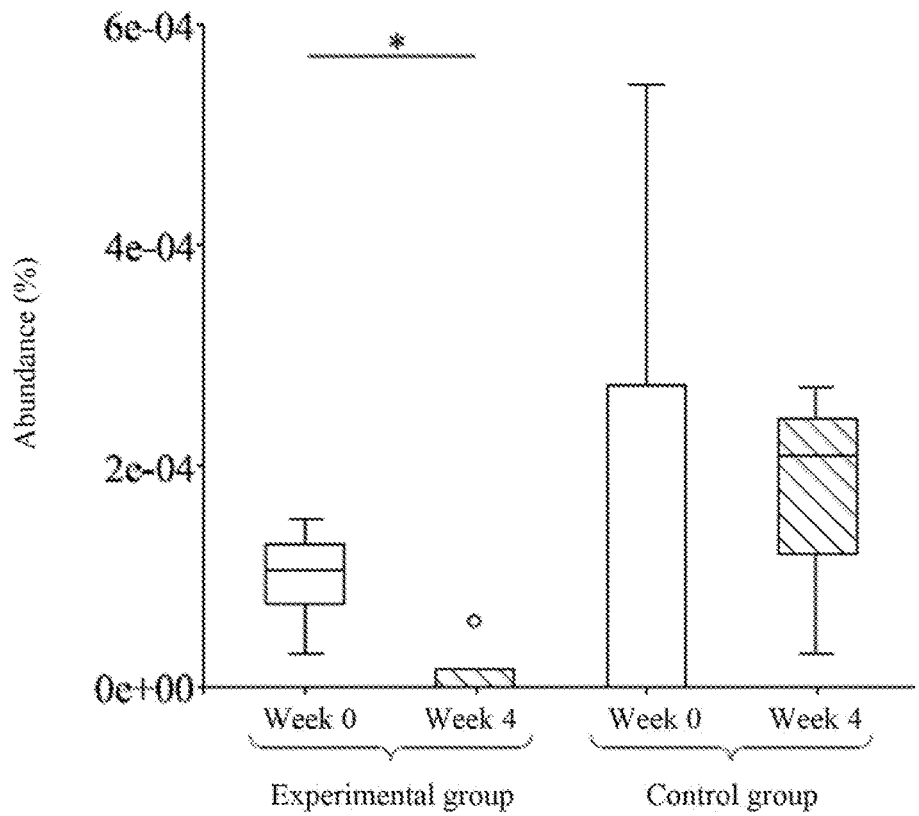
FIG. 13 is a graph showing an analysis result of abundance of Intestinibacter bacteria at week 0 and week 4.

Referring to FIG. 13, in the experimental group at week 0, the four subjects had the abundances of the Intestinibacter bacteria between $5\times10^{-5}$% and $2'10^{-4}$% with an average abundance of $9.83\times10^{-5}$% and an abundance median of $1.1\times10^{-4}$%; in the control group at week 0, the three subjects had the abundances of the Intestinibacter bacteria between 0.00% and $3\times10^{-4}$% with an average abundance of $1.8\times10^{-4}$% and an abundance median of 0.00%. The seven subjects after 4 weeks of taking the capsules for each group had different changes in gut microbiota. In the experimental group at week 4, the four subjects had the abundances of the Intestinibacter bacteria between 0.00% and $5\times10^{-5}$% with an average abundance of $1.51\times10^{-5}$% and an abundance median of 0.00%; in the control group at week 4, the three subjects had the abundances of the Intestinibacter bacteria between $1.0\times10^{-4}$% and $3\times10^{-4}$% with an average abundance of $1.7\times10^{-4}$% a and an abundance median of $2.1\times10^{-4}$%.

It can be learned that the subjects to whom the composition containing the *Lactiplantibacillus plantarum* TCI837 and iron supplement was administered for 4 weeks in the experimental group had the average abundance of the Intestinibacter bacteria reduced to $1.51\times10^{-5}$%, and the subjects to whom only the iron supplement was administered for 4 weeks in the control group have the average abundance of the Intestinibacter bacteria maintained at $1.7\times10^{-4}$%, indicating that the iron supplement with *Lactiplantibacillus plantarum* TCI837 help significantly reduced the Intestinibacter bacteria in the intestine, thereby reducing the possibility of sleep disorders.

Figure 14:
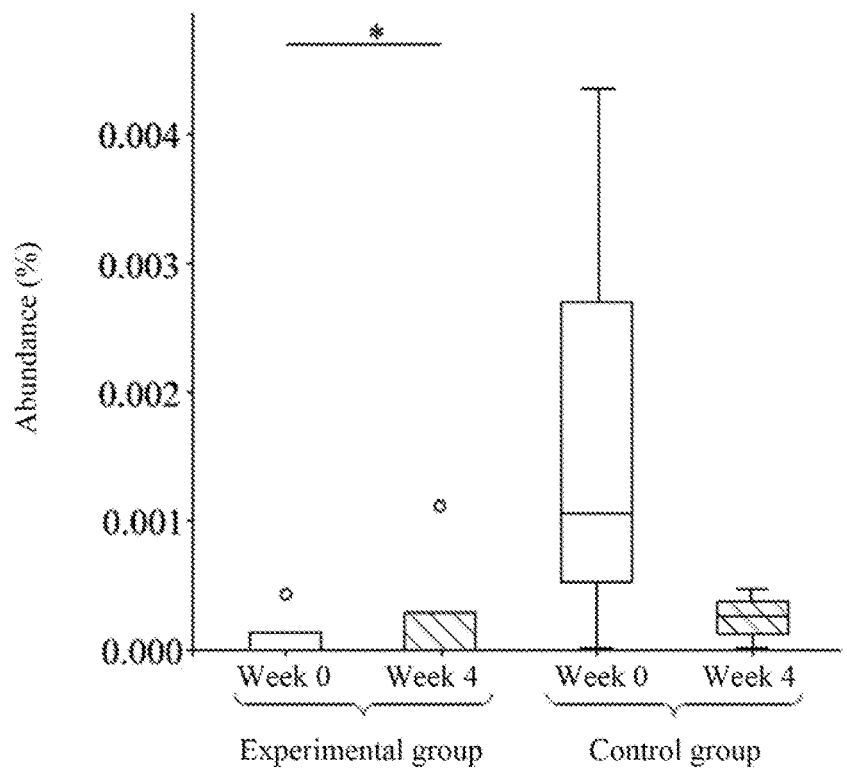
FIG. 14 is a graph showing an analysis result of abundance of Lachnospiraceae NK4A136 group bacteria at week 0 and week 4.

Referring to FIG. 14, in the experimental group at week 0, the four subjects had the abundances of the Lachnospiraceae NK4A136 group bacteria between 0.00% and $2.5\times10^{-4}$% with an average abundance of $1.1\times10^{-4}$% and an abundance median of 0.00%; in the control group at week 0, the three subjects had the abundances of the Lachnospiraceae NK4A136 group bacteria between $5\times10^{-4}$% and $3\times10^{-3}$% with an average abundance of $1.8\times10^{-3}$% and an abundance median of $1.1\times10^{-3}$%. The seven subjects after 4 weeks of taking the capsules for each group had different changes in gut microbiota. In the experimental group at week 4, the four subjects had the abundances of the Lachnospiraceae NK4A136 group bacteria between 0.00% and $5\times10^{-4}$% with an average abundance of $2.8\times10^{-4}$% and an abundance median of 0.00%; in the control group at week 4, the three subjects had the abundances of the Lachnospiraceae NK4A136 group bacteria between 0.00% and $5\times10^{-4}$% with an average abundance of $2.4\times10^{1}$% and an abundance median of $2.7\times10^{-4}$%.

It can be learned that the subjects to whom the composition containing the *Lactiplantibacillus plantarum* TCI837 and iron supplement was administered for 4 weeks in the experimental group had the average abundance of the Lachnospiraceae NK4A136 group bacteria increased to $2.8\times10^{-4}$%, and the subjects to whom only the iron supplement was administered for 4 weeks in the control group had the average abundance of the Lachnospiraceae NK4A136 group bacteria reduced from $1.8\times10^{-3}$% to $2.4\times10^{-4}$%, indicating that the iron supplement with *Lactiplantibacillus plantarum* TCI837 helped significantly increase the Lachnospiraceae NK4A136 group bacteria in the intestine, thereby increasing the possibility of intestinal barrier function.

Figure 15:
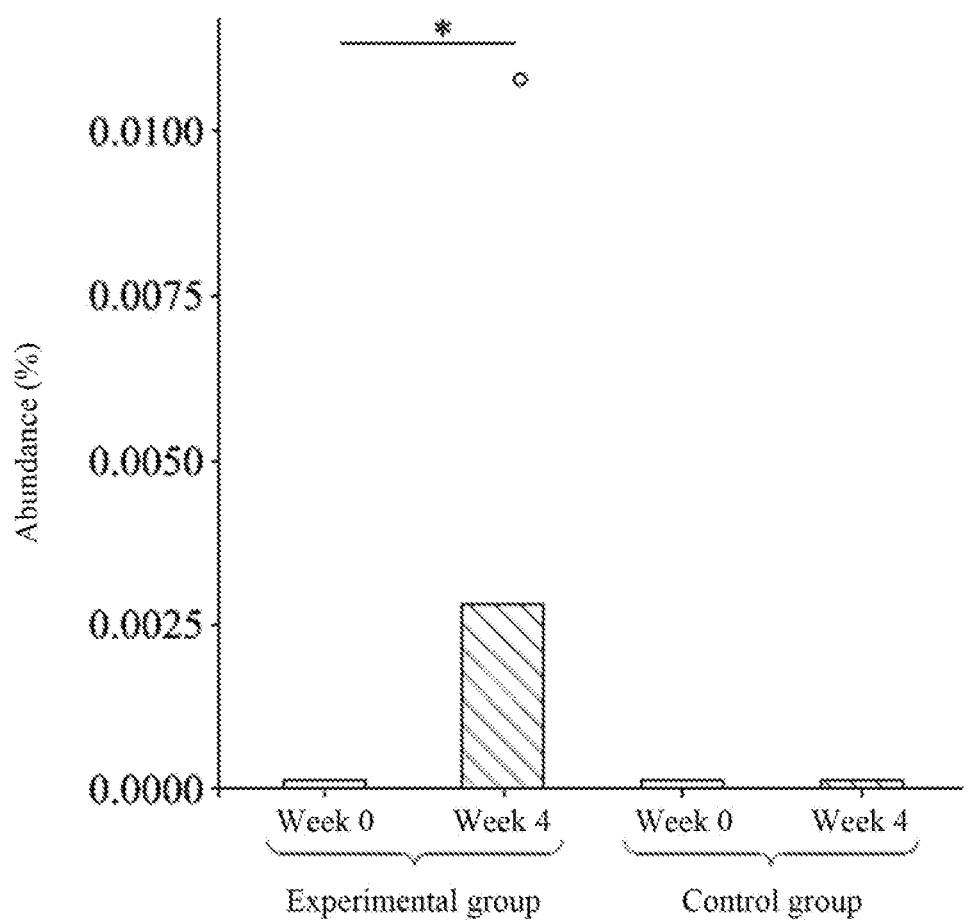
FIG. 15 is a graph showing an analysis result of abundance of Lachnospiraceae [*Eubacterium*] *ruminantium* group bacteria at week 0 and week 4.

Referring to FIG. 15, in the experimental group at week 0, the four subjects had the abundances of the Lachnospiraceae [*Eubacterium*] *ruminantium* group bacteria around 0.00% with an average abundance of 0.00% and an abundance median of 0.00%; in the control group at week 0, the three subjects had the abundances of the Lachnospiraceae [*Eubacterium*] *ruminantium* group bacteria around 0.00% with an average abundance of 0.00% and an abundance median of 0.00%. The seven subjects after 4 weeks of taking the capsules for each group had different changes in gut microbiota. In the experimental group at week 4, the four subjects had the abundances of the Lachnospiraceae [*Eubacterium*]*ruminantium* group bacteria between 0.00% and 0.003% with an average abundance of $2.7 \times 10^{-3}$% and an abundance median of $1.51 \times 10^{-5}$%; in the control group at week 4, the three subjects had the abundances of the Lachnospiraceae [*Eubacterium*] *ruminantium* group bacteria around 0.00% with an average abundance of 0.00% and an abundance median of 0.00%.

It can be learned that the subjects to whom the composition containing the *Lactiplantibacillus plantarum* TCI837 and iron supplement was administered for 4 weeks in the experimental group had the average abundance of the Lachnospiraceae [*Eubacterium*]*ruminantium* group bacteria increased to $2.7 \times 10^{-3}$%, and the subjects to whom only the iron supplement was administered for 4 weeks in the control group have the average abundance of the Lachnospiraceae [*Eubacterium*] *ruminantium* group bacteria unchanged, indicating that the iron supplement with *Lactiplantibacillus plantarum* TCI837 help significantly increased the Lachnospiraceae [*Eubacterium*] *ruminantium* group bacteria, thereby maintaining intestinal health.

In summary, *Lactiplantibacillus plantarum* TCI837 according to any embodiment of the present invention can be used to prepare a composition for supplementing iron, promoting the absorption of iron in a subject, and/or improving the gut microbiota (such as promoting or inhibiting the growth of Enterobacteriaceae bacteria, *Campylobacter* bacteria, Intestinibacter bacteria, Lachnospiraceae NK4A136 group bacteria, and Lachnospiraceae [*Eubacterium*] *ruminantium* group bacteria) of a subject. In addition, an iron supplement composition containing *Lactiplantibacillus plantarum* TCI837 and an iron supplement of any embodiment can be used to supplement iron. A composition of any embodiment contains *Lactiplantibacillus plantarum* TCI837 to increase the content of ferritin in a subject, reduce the total iron-binding capacity of serum in a subject, increase the content of red blood cells in a subject, increase the content of heme in a subject, increase the hematocrit of a subject, and relieve the discomfort resulting from iron-deficiency anemia in a subject experiencing symptoms of iron-deficiency anemia. A composition of any embodiment contains *Lactiplantibacillus plantarum* TCI837 to improve the gut microbiota in a subject and to increase probiotics and reduce non-probiotics, thereby delaying the occurrence of an intestinal disease, improving intestinal barrier functions of the subject, and maintaining intestinal health of the subject. A composition of any embodiment contains an effective dose of 50 mg/day of the *Lactiplantibacillus plantarum* TCI837.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A method for supplementing iron and/or promoting absorption of iron in a subject in need thereof, comprising administering to the subject a composition comprising an effective dose of *Lactiplantibacillus plantarum* TCI837 deposited in Leibniz Institute DSMZ under an accession number of DSM 33843.

2. The method according to claim 1, wherein promoting absorption of iron in the subject in need thereof comprises increasing a content of ferritin in the subject, reducing a total iron-binding capacity of serum in the subject, increasing a content of red blood cells in the subject, increasing a content of heme in the subject, increasing a content of hematocrit of the subject, or a combination thereof.

3. The method according to claim 1, wherein when the subject is experiencing symptoms of iron-deficiency anemia, the *Lactiplantibacillus plantarum* TCI837 reduces the symptoms of iron-deficiency anemia, wherein the symptoms of iron-deficiency anemia comprise cold hands and feet, cramps, hyposthenia, dizziness caused by changing postures, dizziness when calm, feeling of weakness, or a combination thereof.

4. The method according to claim 1, wherein the effective dose is 50 mg/day of the *Lactiplantibacillus plantarum* TCI837.

5. The method according to claim 1, wherein the composition further comprises an effective dose of an iron supplement.

6. The method according to claim 5, wherein the iron supplement is ferrous gluconate, and a weight ratio of the *Lactiplantibacillus plantarum* TCI837 to the ferrous gluconate is 1:3.2.

* * * * *

SEQUENCE LISTING

<160> NUMBER OF SEQ ID NOS: 4

<210> SEQ ID NO 1
<211> LENGTH: 1271
<212> TYPE: DNA
<213> ORGANISM: Lactobacillus plantarum

<400> SEQUENCE: 1

```
caatcctgtc acattaggcg gctggttcct aaaaggttac cccaccgact ttgggtgtta      60
caaactctca tggtgtgacg ggcggtgtgt acaaggcccg ggaacgtatt caccgcggca     120
tgctgatccg cgattactag cgattccgac ttcatgtagg cgagttgcag cctacaatcc     180
gaactgagaa tggctttaag agattagctt actctcgcga gttcgcaact cgttgtacca     240
tccattgtag cacgtgtgta gcccaggtca taagggcat gatgatttga cgtcatcccc      300
accttcctcc ggtttgtcac cggcagtctc accagagtgc ccaacttaat gctggcaact     360
gataataagg gttgcgctcg ttgcgggact taacccaaca tctcacgaca cgagctgacg     420
acaaccatgc accacctgta tccatgtccc cgaagggaac gtctaatctc ttagatttgc     480
atagtatgtc aagacctggt aaggttcttc gcgtagcttc gaattaaacc acatgctcca     540
ccgcttgtgc gggcccccgt caattccttt gagtttcagc cttgcggccg tactccccag     600
gcggaatgct taatgcgtta gctgcagcac tgaagggcgg aaaccctcca acacttagca     660
ttcatcgttt acggtatgga ctaccagggt atctaatcct gtttgctacc catactttcg     720
```

| | |
|---|---:|
| agcctcagcg tcagttacag accagacagc cgccttcgcc actggtgttc ttccatatat | 780 |
| ctacgcattt caccgctaca catggagttc cactgtcctc ttctgcactc aagtttccca | 840 |
| gtttccgatg cacttcttcg gttgagccga aggctttcac atcagactta aaaaaccgcc | 900 |
| tgcgctcgct ttacgcccaa taaatccgga caacgcttgc cacctacgta ttaccgcggc | 960 |
| tgctggcacg tagttagccg tggctttctg gttaaatacc gtcaatacct gaacagttac | 1020 |
| tctcagatat gttcttcttt aacaacagag tttacgagcc gaaacccttc tcactcacgc | 1080 |
| gcgtgctcat cagacttcgt cccaatgtga agatccctac tgctgctctc ccgtaaagaa | 1140 |
| gttggccgtg tctcagttcc caatggtagc gaatacccte tcagtccgcc tacagtatca | 1200 |
| ttggccaatg ggtgagcgct aatctcacca tctagctaat ataagcccgc cgaacacatc | 1260 |
| tctctcacaa a | 1271 |

<210> SEQ ID NO 2
<211> LENGTH: 1202
<212> TYPE: DNA
<213> ORGANISM: Lactobacillus plantarum

<400> SEQUENCE: 2

| | |
|---|---:|
| gcccattggg gcttgcctaa tacatgcatg tcgaacgaac tctggtattg attggtgctt | 60 |
| gcatcatgat ttacatttga gtgagtggcg aactggtgag taacacgtgg gaaacctgcc | 120 |
| cagaagcggg ggataacacc tggaaacaga tgctaatacc gcataacaac ttggaccgca | 180 |
| tggtccgagc ttgaaagatg gcttcggcta tcacttttgg atggtcccgc ggcgtattag | 240 |
| ctagatggtg gggtaacggc tcaccatggc aatgatacgt agccgacctg agagggtaat | 300 |
| cggccacatt gggactgaga cacggcccaa actcctacgg gaggcagcag tagggaatct | 360 |
| tccacaatgg acgaaagtct gatggagcaa cgccgcgtga gtgaagaagg gtttcggctc | 420 |
| gtaaaactct gttgttaaag aagaacatat ctgagagtaa ctgttcaggt attgacggta | 480 |
| tttaaccaga aagccacggc taactacgtg ccagcagccg cggtaatacg taggtggcaa | 540 |
| gcgttgtccg gatttattgg gcgtaaagcg agcgcaggcg gttttttaag tctgatgtga | 600 |
| aagccttcgg ctcaaccgaa gaagtgcatc ggaaactggg aaacttgagt gcagaagagg | 660 |
| acagtggaac tccatgtgta gcggtgaaat gcgtagatat atggaagaca ccagtggcga | 720 |
| aggcggctgt ctggtctgta actgacgctg aggctcaaaa gtatgggtag caaacaggat | 780 |
| tagatacccct ggtagtccat accgtaaacg atgaatgctt agtgtaggag ggtttccgcc | 840 |
| cttcagtgct gcaactaacg caataagcat tcccgcctgg aggaagtacg gcccgcaagg | 900 |
| ctgaaaactc aaaagaattg acgggcgccc gcacaagcg gtggagcat ggttgtttta | 960 |
| attagaagct acgcgaagca tctttacagg ttctgacata ctatgcaatc taagaagaat | 1020 |
| agaatgttcc cttcggaaca tgaaatacag ggggtgcatg ttgtcgtcag ctcggtctga | 1080 |
| aatgttggat aagtcccgca cgagccacct tataatcagt gcagcatagt gcactctgtg | 1140 |
| aactgcgtac aacgagacag tgcaacctca attcatatgc cttacgacct ggctacaaac | 1200 |
| gt | 1202 |

<210> SEQ ID NO 3
<211> LENGTH: 1121
<212> TYPE: DNA
<213> ORGANISM: Lactobacillus plantarum

<400> SEQUENCE: 3

| | |
|---|---:|
| ggataattcc ctatcatagt aatacatgca agtcgaacga actctggtat tgattggtgc | 60 |

```
ttgcatcatg atttacattt gagtgagtgg cgaactggtg agtaacacgt gggaaacctg      120
cccagaagcg ggggataaca cctggaaaca gatgctaata ccgcataaca acttggaccg      180
catggtccga gtttgaaaga tggcttcggc tatcactttt ggatggtccc gcggcgtatt      240
agctagatgg tggggtaacg gctcaccatg gcaatgatac gtagccgacc tgagagggta      300
atcggccaca ttgggactga cacggccc aaactcctac gggaggcagc agtagggaat       360
cttccacaat ggacgaaagt ctgatggagc aacgccgcgt gagtgaagaa gggtttcggc      420
tcgtaaaact ctgttgttaa agaagaacat atctgagagt aactgttcag gtattgacgg      480
tatttaacca gaaagccacg gctaactacg tgccagcagc cgcggtaata cgtaggtggc      540
aagcgttgtc cggatttatt gggcgtaaag cgagcgcagg cggttttta agtctgatgt       600 gaaagccttc ggctcaaccg aagaagtgca tcggaaactg gaaacttga gtgcagaaga      660 ggacagtgga actccatgtg tagcggtgaa atgcgtagat atatggaaga acaccagtgg      720
cgaaggcggc tgtctggtct gtaactgacg ctgaggctcg aaagtatggg tagcaaacag      780
gattagatac cctggtagtc cataccgtaa acgatgaatg ctaagtgttg gagggtttcc      840
gcccttcagt gctgcagcta acgcattaag cattccgcct ggggagtacg gccgcaaggc      900
tgaaactcaa aggaattgac ggggccccgc acaagcggtg gagcatgtgg tttaattcga      960
agctacgcga agaaccttac agtcttgaca tactatgcaa atctagagat tagacgttcc     1020
cttcggggac atgatacagt gtgcatgatg tcgtcagctc gtgtcgtgag attgttggta     1080
gtcccgcaac gagcgcatcc tttatttatc agttgccagc a                         1121
```

<210> SEQ ID NO 4
<211> LENGTH: 1222
<212> TYPE: DNA
<213> ORGANISM: Lactobacillus plantarum

<400> SEQUENCE: 4

```
tagggcgggc ggcggctata catgcaagtc gaacgaactc tggtattgat tggtgcttgc       60
atcatgattt acatttgagt gagtggcgaa ctggtgagta acacgtggga aacctgccca      120
gaagcggggg ataacacctg gaaacagatg ctaataccgc ataacaactt ggaccgcatg      180
gtccgagttt gaaagatggc ttcggctatc acttttggat ggtcccgcgg cgtattagct      240
agatggtggg gtaacggctc accatggcaa tgatacgtag ccgacctgag agggtaatcg      300
gccacattgg gactgagaca cggcccaaac tcctacggga gcagcagta gggaatcttc       360 cacaatggac gaaagtctga tggagcaacg ccgcgtgagt gaagagggt tcggctcgt        420 aaaactctgt tgttaaagaa gaacatatct gagagtaact gttcaggtat tgacggtatt     480
taaccagaaa gccacggcta actacgtgcc agcagccgcg gtaatacgta ggtggcaagc      540
gttgtccgga tttattgggc gtaaagcgag cgcaggcggt tttttaagtc tgatgtgaaa      600
gccttcggct caaccgaaga gtgcatcgg aaactgggaa acttgagtgc agaagaggac       660
agtggaactc catgtgtagc ggtgaaatgc gtagatatat ggaagaacac cagtggcgaa      720
ggcggctgtc tggtctgtaa ctgacgctga ggctcgaaag tatgggtagc aaacaggatt     780
agataccctg gtagtccata ccgtaaacga tgagtgctaa gtgttgggag ggtttccgcc      840
cttcagtgct gcagctaacg cattaagcat tccgcctggg ggagtacggc cgcaaggctg      900
aactcaaagg aattgacggg gggcccgcac aagcggtgga gcatgtggt ttaattcgaa       960 gcttacgcga agacctacca ggtcttgaca tactatggca atctaaaaga atagacgttc     1020
```

```
ctttcgggga catggaatac agggtggtgg catggtggtg tcagcctcgt ccgtgaaatg    1080
gtgggtaagt tcccgctacg aggcccaccc tatatatcgt ggcaagcatt agttgggcac    1140
ttggttggaa ctgcgtgtac gacgggaggc agggtgggtc agtactcaat catcaatggt    1200
cctatagagc cttggggtac ta                                             1222
```